United States Patent
Baker

(10) Patent No.: US 11,639,332 B2
(45) Date of Patent: May 2, 2023

(54) METHODS AND COMPOSITIONS OF ISOINDOLINE-1,3-DIONE AND ISOINDOLE PRODRUGS USEFUL FOR TREATING CANCER, ULCERATIVE COLITIS AND RELATED INFLAMMATORY DISEASES

(71) Applicant: AMGEN (EUROPE) GMBH, Risch-Rotkreuz (CH)

(72) Inventor: William R. Baker, Bellevue, WA (US)

(73) Assignees: AMGEN (EUROPE) GMBH, Risch-Rotkreuz (CH); PRO-ONICS PHARMACEUTICALS LLC

( * ) Notice: Subject to any disclaimer, the term of this patent is extended or adjusted under 35 U.S.C. 154(b) by 0 days.

(21) Appl. No.: 16/970,598

(22) PCT Filed: Mar. 6, 2019

(86) PCT No.: PCT/EP2019/055576
§ 371 (c)(1),
(2) Date: Aug. 17, 2020

(87) PCT Pub. No.: WO2019/170750
PCT Pub. Date: Sep. 12, 2019

(65) Prior Publication Data
US 2020/0392082 A1    Dec. 17, 2020

Related U.S. Application Data

(60) Provisional application No. 62/639,650, filed on Mar. 7, 2018.

(51) Int. Cl.
| C07D 209/48 | (2006.01) |
| A61P 1/04 | (2006.01) |
| C07C 245/06 | (2006.01) |
| C07D 401/04 | (2006.01) |
| A61K 9/00 | (2006.01) |

(52) U.S. Cl.
CPC .......... *C07D 209/48* (2013.01); *A61K 9/0053* (2013.01); *A61P 1/04* (2018.01); *C07C 245/06* (2013.01); *C07D 401/04* (2013.01)

(58) Field of Classification Search
CPC ................ C07D 209/48; A61P 1/04
See application file for complete search history.

(56) References Cited

U.S. PATENT DOCUMENTS

| 3,951,943 | A |  | 4/1976 | Towle |  |
| 6,822,159 | B2 | * | 11/2004 | Ikeda | H01L 51/005 |
|  |  |  |  |  | 257/431 |
| 7,182,953 | B2 |  | 2/2007 | Zeldis |  |
| 7,325,355 | B2 |  | 2/2008 | Zeldis |  |
| 8,853,175 | B2 |  | 10/2014 | Kumar et al. |  |
| 9,334,305 | B2 | * | 5/2016 | Schteingart | A61P 27/02 |
| 2,472,965 | A1 |  | 6/2019 | Wehrli |  |

FOREIGN PATENT DOCUMENTS

| EP | 0856562 A1 | 8/1998 |
| WO | 2009/120167 A1 | 10/2009 |
| WO | 2012/083153 A1 | 6/2012 |
| WO | 2012/096884 A1 | 7/2012 |

OTHER PUBLICATIONS

Harveer et al., Synthesis, characterization and radical scavenging activity of aromatic amine conjugates of 5-aminosalicylic acid, Bull. Chem. Soc. Eth., 28(3):475-480 (2014).
Hassan et al., Design, synthesis and anti-ulcerogenic effect of some of furo-salicylic acid derivatives on acetic acid-induced ulcerative colitis, Eur. J. Med. Chem., 45(9):4104-4112 (2010).
International Application No. PCT/EP2019/055576, International Search Report and Written Opinion, dated May 27, 2019.
International Application No. PCT/EP2019/055576, International Preliminary Report on Patentability, dated Sep. 17, 2020.
Kruis et al., Low dose balsalazide (1.5 g twice daily) and mesalazine (0.5 g three times daily) maintained remission of ulcerative colitis but high dose balsalazide (3.0 g twice daily) was superior in preventing relapses, Gut., 49(6):783-789 (2001).
Loher et al., The specific type-4 phosphodiesterase inhibitor mesopram alleviates experimental colitis in mice, J. Pharmacol. Exp. Ther., 305:549-556 (2003).
Maeda et al., Effects of intravenous and oral administration of OPC-6535 in a rat model of 2,4,6-trinitro benzene sulfonic acid (TNBS)-induced colitis. Gut 41 (suppl 3), AI 12, (1997).
Man et al., Discovery of (S)-N-[2-[1-(3-ethoxy-4-methoxyphenyl)-2-methanesulfonylethyl]-1,3-dioxo-2,3-dihydro-1H-isoindol-4-yl] acetamide (apremilast), a potent and orally active phosphodiesterase 4 and tumor necrosis factor-alpha inhibitor, J. Med. Chem., 52:1522-1524 (2009).

(Continued)

*Primary Examiner* — Kamal A Saeed
(74) *Attorney, Agent, or Firm* — Marshall, Gerstein & Borun LLP

(57) ABSTRACT

Provided herein are azo prodrugs of small-molecule isoindoline-1,3-diones and isoindoles anti-inflammatory inhibitors according to formula IA, in particular PDE4 inhibitors, which prodrugs can be administered orally to a subject in need thereof, whereby the prodrugs are cleaved in the colon and the PDE4 inhibitor released.

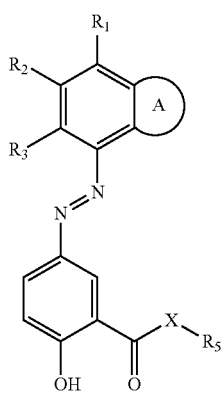

IA

9 Claims, 8 Drawing Sheets

(56) References Cited

OTHER PUBLICATIONS

Muller et al., Amino-substituted thalidomide analogs: potent inhibitors of TNF-@a production, Bio. Med Chem .Lett., 9(11):1625-1630 (1999).
Odingo, Inhibitors of PDE4: a review of recent patent literature, Exp. Opin. Ther. Pat., 15:773-787 (2005).
Papadakis et al., Role of cytokines in the pathogenesis of inflammatory bowel disease, Annu. Rev. Med., 51:289-298 (2000).
Puig et al., Curative effects of phosphodiesterase 4 inhibitors in dextra sulfate sodium-induced colitis in the rat, Gastroenterology, 114, G4357 (1998).
Reichel, Componenta de separare in sinteza colorantilor vii. Spectre de absorbtie ale unor co-oranti, Azoici, Cu Par.Tticipar.Ea Componentelor Centrale Naftalin-1,5—I 1,4-Disazoice, Stu.SI Cer. Stin. Ser. I, 4:51-63 (1957).
Suneela et al., Azo Reductase-Activated Colon-Targeting Prodrugs of Aminosalicylates for Inflammatory Bowel Disease: reparation, Pharmacokinetic and Pharmacodynamic Profile, Inflam. Aller. Dru. Tar., 12(6):419-432 (2013).
Videla et al., Selective inhibition of phosphodiesterase type IV ameliorates chronic colitis and prevents intestinal fibrosis, Gastroenterology, 114, G4542 (1998).

\* cited by examiner

METHODS AND COMPOSITIONS OF ISOINDOLINE-1,3-DIONE AND ISOINDOLE PRODRUGS USEFUL FOR TREATING CANCER, ULCERATIVE COLITIS AND RELATED INFLAMMATORY DISEASES

FIELD

The present disclosure relates to a novel class of anti-inflammatory small-molecule prodrugs of a PDE4 benzophenone inhibitor of IL-1β, and TNF-α. These novel prodrugs are activated by colonic bacteria that reside in the large intestine thereby releasing both the small-molecule anti-inflammatory PDE4 inhibitor and 5-aminosalacyclic acid at the site of inflammatory disease, the lamina propria. The novel prodrugs and methods provide an effective treatment modality for cancer, plaque psoriasis, psoriatic arthritis, inflammatory bowel disease, Crohn's disease, and ulcerative colitis.

BACKGROUND

Ulcerative Colitis (UC) is a disease of the colon that includes characteristic ulcers or open sores, occurring in 35-100 people for every 100,000 people in the US. UC is characterized by chronic relapsing inflammation of the gastrointestinal tract that arises from inappropriate activation of the mucosal immune system. An imbalance between pro- and anti-inflammatory cyctokines that is present in U C leads to the destruction of normal tissue integrity (Papadakis K A, Targan S R, "Role of cyctokines in the pathogenesis of inflammatory bowel disease". Annual Rev. Med. 2000; 51: 289-98). Treatment of UC typically involves administration of anti-inflammatory drugs to arrest the underlying inflammation associated with the disease by inhibition of pro-inflammatory cyctokines. Drugs from four unique classes are generally employed, they are: aminosaliscylates, glucocorticoids, immunomodulators and anti-TNF biologics. 5-aminosalacyclic acid and its azo prodrugs are widely used and are positioned as first line treatment. An example of azo prodrugs include osalazine, balsalazide and sulfasalazine. All three of these prodrugs are approved to treat inflammation associated with ulcerative colitis (UC). (Kruis, W.; Schreiber, I.; Theuer, D.; Brandes, J. W.; Schutz, E.; Howaldt, S.; Krakamp, B.; Hämling, J.; Monnikes, H.; Koop, I.; Stolte, M.; Pallant, D.; Ewald, U. "Low dose balsalazide (1.5 g twice daily) and mesalazine (0.5 g three times daily) maintained remission of ulcerative colitis but high dose balsalazide (3.0 g twice daily) was superior in preventing relapses". *Gut* 2001, 49 (6): 783-789.). The azo prodrugs efficiently release the anti-inflammatory drug, 5-aminosalacyclic acid, upon activation (prodrug reduction) by enteric bacteria residing in the colon. In the case of balsalazide and sulfasalazine, the inactive side products, 3-(4-amino-benzoylamino)-propionic acid and sulfapyridine, are also released, respectively. An additional benefit of sulfasalazine is that it passes unmodified through the upper gastrointestinal tract until it reaches the colon where it is metabolized. Sulfasalazine's main mode of action is therefore believed to be achieved by topical administration inside the intestine. Glucocorticoids whether systemic (prednisone) or topical (budesonide, Entocort) are currently used to suppress inflammation in UC and these drugs are very effective in treating the underlining inflammation. Unfortunately, glucocorticoid therapy is fraught with serious side effects to include hypothalamic-pituitary-adrenal axis insufficiency, osteoporosis, diabetes, steroid myopathy and infectious and neuropsychiatric complications, thus limiting their broad use especially in elderly patients. Due to these serious side effects topical preparations via rectal administration (suppository) have been developed. Immunomodulators such as mercaptopurine, methotrexate, azathioprine and cyclosporine are usually reserved for patients with unresponsive disease and for maintaining remission. Thus, the immunomodulators are reserved as a second-line treatment option due to their severe immunosuppressive effects. Anti-TNF biologics such as Adalimumab (Humira), cerolizumab (Cimzia), golimumab (Simponi), and infliximab (Remicade) target specific components of the immune response, namely TNFα and its receptors. Biologics although effective in inducing and maintaining remission, are expensive and require parental administration. Additionally, these drugs suppress the immune system sufficiently to warrant concern for bacterial/viral infection of patients who receive this therapy.

Untreated or ineffective treatment of UC can lead to colon cancer and in certain instances patients will require colectomy, a partial or total removal of the large bowel. This aggressive surgical procedure is necessary to arrest the disease and while effective, the procedure renders the patient unable to remove water from stool. It is now clear that newer and more effective treatment modalities for UC are needed.

The phosphodiesterase 4 (PDE4) is an important member of a large PDE family of enzymes. PDE4 is a specific cyclic adenosine monophosphatase (cAMP) which converts in the cell cAMP to AMP. Thus inhibition of cAMP conversion to AMP (inhibition of PDE4) raises intracellular levels of cAMP thereby influencing multiple intracellular signaling pathways (Odingo, J. O. Inhibitors of PDE4: a review of recent patent literature. *Exp. Opin. Ther. Pat.* 2005, 15, 773-787). One major consequence of elevated cAMP is the blockade of tumor necrosis factor-α (TNF-α), a key cytokine in the inflammatory cascade. Elevated levels of TNF-α have been associated with numerous inflammatory diseases including inflammatory bowel disease, specifically ulcerative colitis. Indeed, PDE4 inhibitors have demonstrated efficacy in animal models of UC (Loher, et al., The specific-type-4phosphodiesterase inhibitor mesopram alleviates experimental colitis in mice. *J. Pharmacol. Exp. Ther.* 2003, 305, 549-556; Maeda, T. et al. Effects of intraveneous and oral administration of OPC-6535 in a rat model of 2,4,6-trinitro benzene sulfonic acid (TNBS)-induced colitis. Gut 41 (suppl. 3), A112, 1997; Puig, J. et al. Curative effects of phosphodiesterase 4 inhibitors in dextra sulfate sodium-induced colitis in the rat Gastroenterology 114, G4357 1998; Videla, S. et al. Selective inhibition of phosphodiesterase type IV ameliorates chronic colitis and prevents intestinal fibrosis. Gastroenterology 114, G4542 1998.

Nausea and emesis appear to be the major adverse events (AE) associated with PDE4 inhibitors, thus these AEs could limit their use to treat IBD or at least limit the effective dose rendering the oral route inefficient. A potential strategy to overcome this limitation would be to a) develop an oral therapeutic that delivers the PDE4 inhibitor directly to the colonic lamina propria avoiding or absorption into the portal circulation and b) design a PDE4 inhibitor therapeutic that when undergoes extensive first-pass metabolism.

There is presently an unmet need for effective treatments for UC with a potent, non- or minimally-absorbed, small-molecule PDE4 inhibitors. Furthermore, topical delivery of a PDE4 inhibitor directly to the colonic lamina propria is a logical strategy to avoid adverse side effects associated with systemic delivery and absorption.

SUMMARY

The present disclosure provides a compound of formula IA:

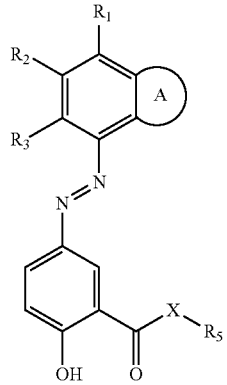

or a pharmaceutically acceptable salt, tautomer or stereoisomer thereof, wherein:

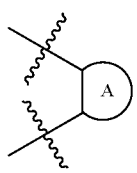

is an optionally substituted 5- or 6-membered carbocyclic ring, an optionally substituted 5- or 6-membered heterocyclic ring, an optionally substituted 5- or 6-membered aryl, or an optionally substituted 5- or 6-membered heteroaryl;

X is independently selected from O, N-alkyl or NH, $R_1$, $R_2$ and $R_3$ are each independently deuterium, hydrogen, halo, alkyl, alkenyl, alkoxy, haloalkyl, cyano, hydroxy, —$NR_6R_7$, or $R_1$ and $R_2$ together with the carbon to which they are attached, join to form an optionally substituted carbocyclic ring, an optionally substituted aryl ring, an optionally substituted heterocyclic ring, or an optionally substituted heteroaryl ring, or $R_2$ and $R_3$, together with the carbon to which they are attached, join to form an optionally substituted carbocyclic ring, an optionally substituted aryl ring, an optionally substituted heterocyclic ring, or an optionally substituted heteroaryl ring;

$R_5$ is hydrogen, alkoxy, alkyl, alkoxyalkyl, wherein $R_5$ is optionally substituted with —$NH_2$, —$NR_6R_7$, —$CO_2H$, or —$(CH_2CH_2O)_n$—$R_{14}$ where n=1-20

$R_6$ and $R_7$ are, at each occurrence, independently hydrogen, alkyl, phenyl, benzyl, or one of $R_6$ or $R_7$ is hydrogen and the other is —$COR_{13}$, or —$SO_2R_{13}$, or $R_6$ and $R_7$ together, with the nitrogen atom to which they are attached, form a heterocyclic or heteroaryl ring comprising moieties selected from the group consisting of carbon, oxygen, nitrogen, sulfur, and $SO_2$;

$R_{13}$ is alkyl, alkenyl, alkynyl, alkoxy, —$NH_2$, or haloalkyl;

$R_{14}$ is —H or alkyl.

In one embodiment, the compound is a compound of formula (I):

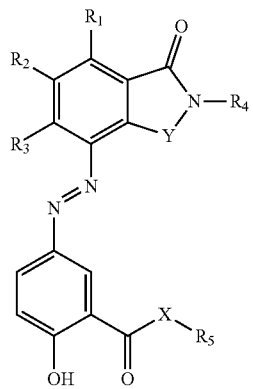

or a pharmaceutically acceptable salt, tautomer, or stereoisomer thereof, wherein:

X is O or NH;

Y is $CH_2$ or C=O;

$R_1$, $R_2$ and $R_3$ are hydrogen or deuterium;

$R_4$ is E or F

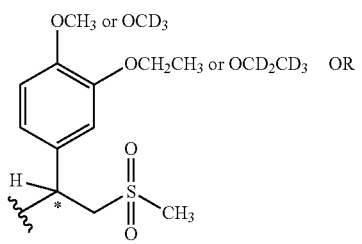

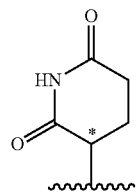

$R^5$ is hydrogen, —$CH_2CO_2H$, —$(CH_2CH_2O)_n$—$CH_3$ and n=1-20.

In a further embodiment, the disclosure provides a compound of formula (II):

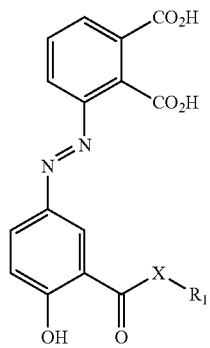

or a pharmaceutically acceptable salt, tautomer or stereoisomer thereof, wherein:
X is O or NH;
$R_1$ is hydrogen, alkyl, branched alkyl, t-butyl, —$CH_2CO_2H$, —$CH_2CO_2CH_3$—$(CH_2CH_2O)_n$—$CH_3$ and n=1-2. One objective of the present disclosure is to provide a non-absorbed azo prodrug of a PDE4 inhibitor that delivers two anti-inflammatory therapeutics to the colon, a PDE4 inhibitor and 5-aminosalacyclic acid (5-ASA):

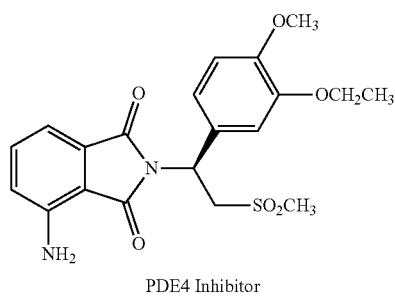

PDE4 Inhibitor

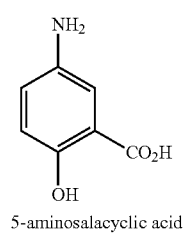

5-aminosalacyclic acid

A second objective of the present disclosure is to develop a prodrug that remains in the GI tract by modification of the prodrug.

Provided herein are thus azo prodrugs of the small-molecule isoindoline-1,3-diones and isoindoles anti-inflammatory inhibitors (U.S. Pat. No. 8,853,175 B2, U.S. Pat. No. 7,182,953 B2, U.S. Pat. No. 7,325,355 B2, Hon-Wah Man et al. *J. Medicinal Chemistry*, 2009, 52, 1522-1524 and related references). When these novel prodrugs are administered orally to experimental animals (rats) in a model of colonic inflammation, the prodrugs are cleaved and release both the PDE4 inhibitor and 5-ASA.

The in vivo efficacy demonstrated in the rat TNBS model of colonic inflammation is the result of the PDE4 inhibitor not 5-ASA. 5-aminosalacyclic acid (5-ASA) is inactive in the TNBS model. Furthermore, the PDE4 inhibitor released from the azo prodrug concentrates in the colonic tissue (lamina propria). Depending on the amount of drug administered, it is now possible to deliver two anti-inflammatory medications to the colon in one molecule.

BRIEF DESCRIPTION OF THE DRAWINGS

The foregoing aspects and many of the attendant advantages of the compounds disclosed herein will become more readily appreciated as the same become better understood by reference to the following detailed description, when taken in conjunction with the accompanying drawings.

DETAILED DESCRIPTION

Figure 1:
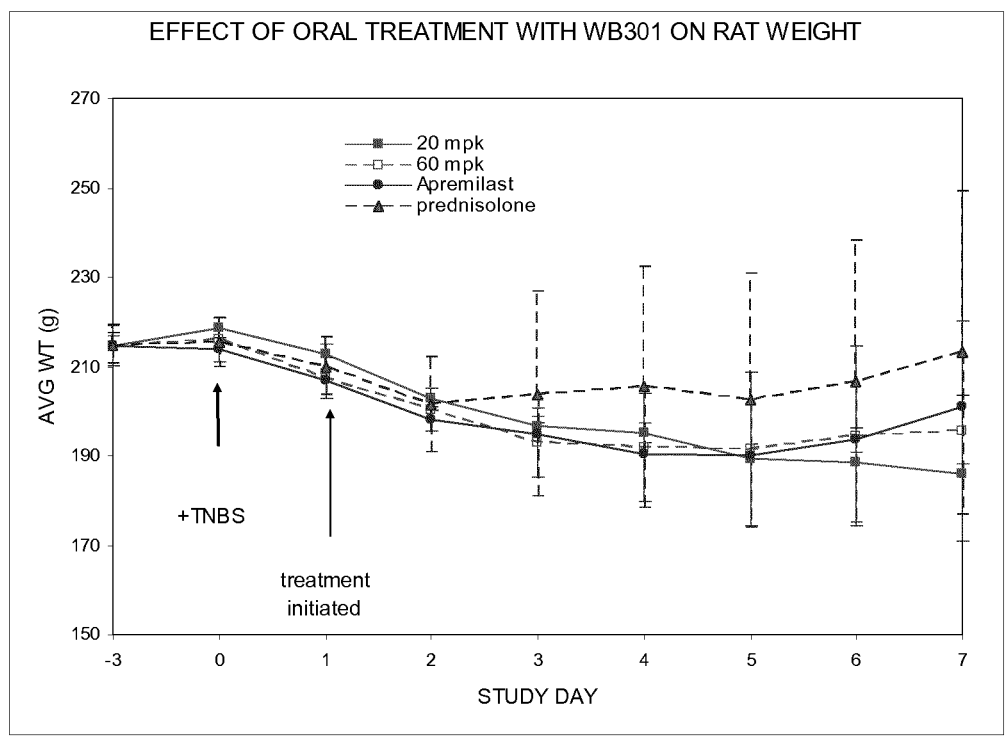
FIG. 1 shows the effect on body weight in an animal model following oral treatments by a prodrug according to one embodiment as compared to other therapy.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In view of the present disclosure, the compounds described herein can be configured by the person of ordinary skill in the art to meet the desired need. In general, the disclosed compounds provide improvements in treatment of cancer, inflammatory bowel disease, Crohn's disease, plaque psoriasis, psoriatic arthritis, and ulcerative colitis.

One embodiment provides a compound having formula IA:

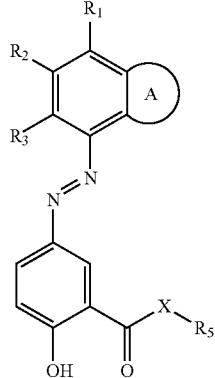

IA or a pharmaceutically acceptable salt, tautomer or stereoisomer thereof, wherein:

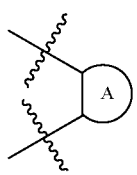

is an optionally substituted 5- or 6-membered carbocyclic ring, an optionally substituted 5- or 6-membered heterocyclic ring, an optionally substituted 5- or 6-membered aryl, or an optionally substituted 5- or 6-membered heteroaryl;

X is independently selected from O, N-alkyl or NH $R_1$, $R_2$ and $R_3$ are each independently deuterium, hydrogen, halo, alkyl, alkenyl, alkoxy, haloalkyl, cyano, hydroxy, —$NR_6R_7$, or $R_1$ and $R_2$ together with the carbon to which they are attached, join to form an optionally substituted carbocyclic ring, an optionally substituted aryl ring, an optionally substituted heterocyclic ring, or an optionally substituted heteroaryl ring, or $R_2$ and $R_3$, together with the carbon to which they are attached, join to form an optionally substituted carbocyclic ring, an optionally substituted aryl ring, an optionally substituted heterocyclic ring, or an optionally substituted heteroaryl ring;

$R_5$ is hydrogen, alkoxy, alkyl, alkoxyalkyl, wherein $R_5$ is optionally substituted with —$NH_2$, —$NR_6R_7$, —$CO_2H$, or —$(CH_2CH_2O)_n$—$R_{14}$ where n=1-20

$R_6$ and $R_7$ are, at each occurrence, independently hydrogen, alkyl, phenyl, benzyl, or one of $R_6$ or $R_7$ is hydrogen and the other is —$COR_{13}$, or —$SO_2R_{13}$, or $R_6$ and $R_7$ together, with the nitrogen atom to which they are attached, form a heterocyclic or heteroaryl ring comprising moieties selected from the group consisting of carbon, oxygen, nitrogen, sulfur, and $SO_2$;

$R_{13}$ is alkyl, alkenyl, alkynyl, alkoxy, —$NH_2$, or haloalkyl; and $R_{14}$ is —H or alkyl.

In certain embodiments,

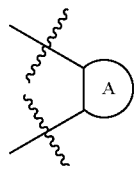

is substituted with one or more $R_4$, wherein $R_4$ has one of the following structures C or D:

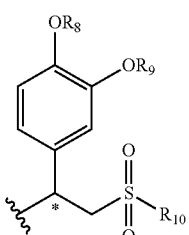

C

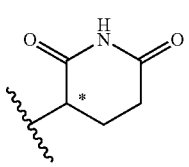

D wherein:
the carbon atom designated * is a stereocenter;
$R_8$ and $R_9$ are, at each occurrence, independently hydrogen, deuterium, alkyl, or deuteroalkyl;
$R_{10}$ is hydroxyl, alkyl, cycloalkyl, cycloalkylalkyl, aralkyl, aryl, or —$NR_{11}R_{12}$;
$R_{11}$ and $R_{12}$ are, at each occurrence, independently hydrogen, alkyl, aryl or aralkyl,
or one of $R_{11}$ or $R_{12}$ is hydrogen and the other is —$COR_{13}$, or —$SO_2R_{13}$,
or $R_{11}$ and $R_{12}$ together, with the nitrogen atom to which they are attached, form a heterocyclic or heteroaryl ring comprising moieties selected from the group consisting of carbon, oxygen, nitrogen, sulfur, and $SO_2$.

One specific embodiment provides compounds of formula I:

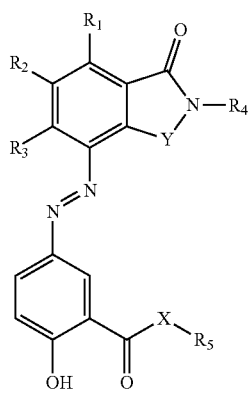

(I)

or a pharmaceutically acceptable salt, tautomer or stereoisomer thereof,
wherein
X is independently selected from O, N-alkyl or NH;
Y is $CH_2$ or $C=O$;
each of $R_1$, $R_2$ and $R_3$, independently of the others, is deuterium, hydrogen, halo, alkyl of 1 to 4 carbons, alkoxy of 1 to 4 carbons, cyano, hydroxy or $-NR_6R_7$; or any of the two of $R_1$, $R_2$, $R_3$ on adjacent carbon atoms, together with the depicted phenylene ring or naphthylidene;
$R_4$ is a radical depicted by formula C or D:

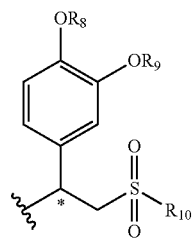

C

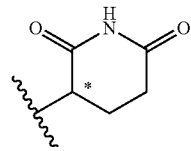

D the carbon atom designated * is a stereocenter;
each of $R_8$ and $R_9$ taken independently of the other is hydrogen, deuterium, alkyl of 1-8 carbons, or deuteroalkyl of 1-8 carbons;
$R_{10}$ is hydroxyl, alkyl of 1-8 carbon atoms, cycloalkyl, $(CH_2)_n$-cycloalkyl, $(CH_2)_n$-phenyl, phenyl, benzyl, or $NR_{11}R_{12}$;
each of $R_{11}$ and $R_{12}$ taken independently of the other, is hydrogen, alkyl of 1-8 carbon atoms, phenyl or benzyl, or one of $R_{11}$ or $R_{12}$ is hydrogen and the other is $-COR_{13}$, or $-SO_2R_{13}$, or $R_{11}$ and $R_{12}$ taken together form a ring of 4-7 atoms of which atoms that make up the ring can be carbon, oxygen, nitrogen and sulfur, and $SO_2$;
$R_5$ is independently selected from a group consisting of hydrogen, alkoxy, alkyl of 1-12 carbons, alkoxyalkyl, $-CH_2CO_2H$, $-(CH_2CH_2O)_n-CH_3$, where n=1-20, alkyl of 1-12 carbons in which the terminal carbon is substituted with $-NH_2$, $-NR_{13}R_{13}$, $-CO_2H$, repeating lengths of $-(CH_2CH_2O)_n-$ where n=1-20; and
each $R_{13}$ is independently alkyl, alkenyl, alkynyl, alkoxy, $-NH_2$, or haloalkyl.

In certain embodiments, a compound within the scope of formula I has the following tautomers A and B:

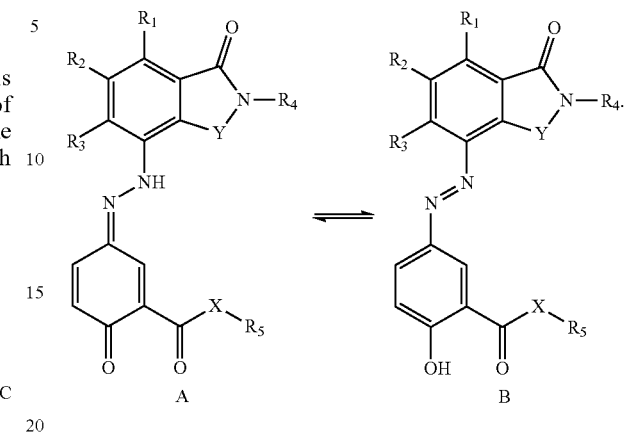

In some embodiments of such compounds are those in which $R_1=R_2=R_3$=hydrogen, $R_4$ is substructure D, Y is $C=O$ and X is O. In further embodiments, $R^5$ is hydrogen, $R_8$ is methyl, $R_9$ is ethyl, and $R_{10}$ is methyl.
In some embodiments of such compounds are those in which $R_1=R_2=R_3$=hydrogen, $R_4$ is substructure D, Y is $CH_2$ and X is O. In further embodiments, $R^5$ is hydrogen, $R_8$ is methyl, $R_9$ is ethyl, and $R_{10}$ is methyl.
In some embodiments of such compounds are those in which $R_1=R_2=R_3$=hydrogen, $R_4$ is substructure C, Y is $C=O$ and X is O. In further embodiments, $R^5$ is hydrogen, $R_8$ is methyl, $R_9$ is ethyl, and $R_{10}$ is methyl.
In some embodiments of such compounds are those in which $R_1=R_2=R_3$=hydrogen, $R_4$ is substructure C, Y is $CH_2$ and X is O. In further embodiments, $R^5$ is hydrogen, $R_8$ is methyl, $R_9$ is ethyl, and $R_{10}$ is methyl.
In some embodiments, $R_1=R_2=R_3$=hydrogen or deuterium. In certain embodiments, $R_1=R_2=R_3$=hydrogen. In some embodiments, X=O or NH. In further embodiments, X=O. In other embodiments, X=NH. In some embodiments, $R_4$ is a radical depicted by formula E or F:

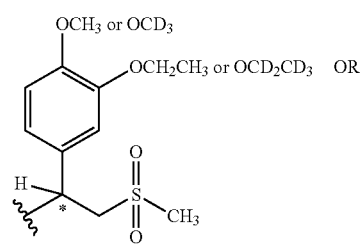

E

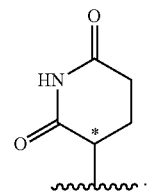

F

In some embodiments, $R^5$ is hydrogen, $-CH_2CO_2H$, $-(CH_2CH_2O)_n-CH_3$ and n=1-20. In other embodiments, $R^5$ is $-(CH_2CH_2O)_n-CH_3$ and n=1-10. In some embodiments, $R_5$=hydrogen and $R_4$ is substructure C, $R_8$ is methyl or $CD_3$, $R_9$ is ethyl or $CD_2CD_3$ and $R_{10}$ is methyl.

In some embodiments, a compound within the scope of formula I or IA has the following tautomeric structures represented by A1 and B1:
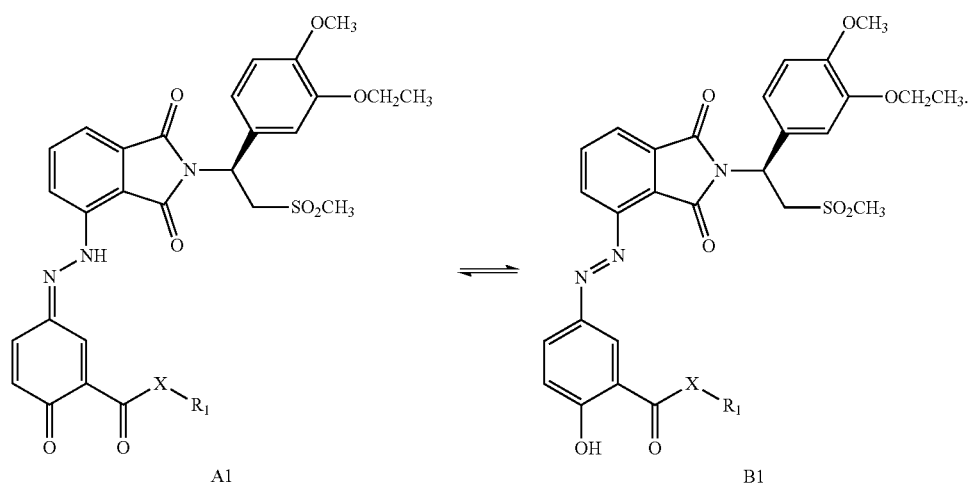
A1 ⇌ B1
In some embodiments, the compound is:
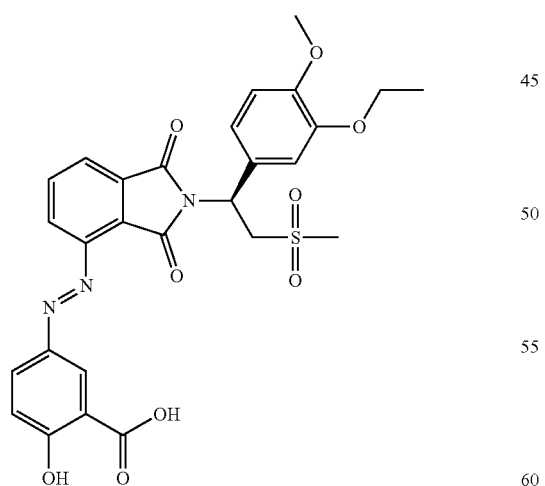
or a pharmaceutically acceptable salt, tautomer or stereoisomer thereof.

In some embodiments, a compound within the scope of formula I has the following tautomers:
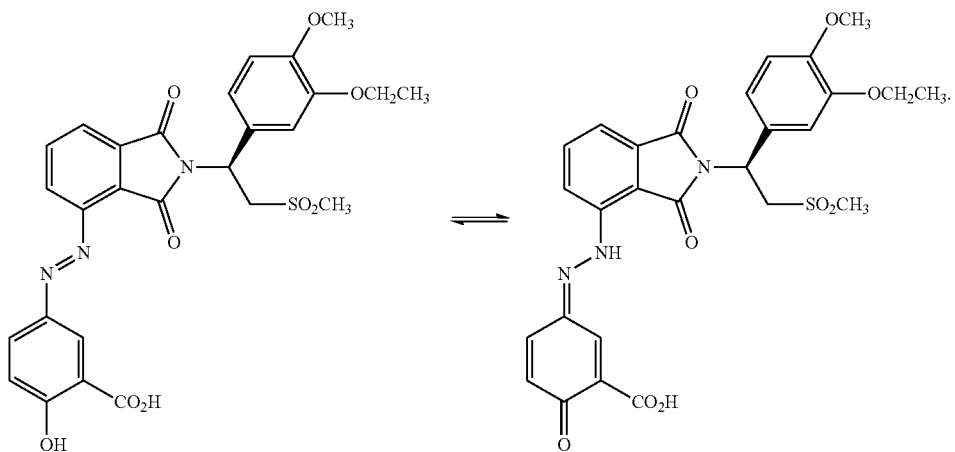 [SMILES: CCOc1cc([C@@H](CS(C)(=O)=O)N2C(=O)c3cccc(/N=N/c4ccc(O)c(C(=O)O)c4)c3C2=O)ccc1OC ; CCOc1cc([C@@H](CS(C)(=O)=O)N2C(=O)c3cccc(N/N=C4/C=CC(=O)C(C(=O)O)=C4)c3C2=O)ccc1OC]
In some embodiments, the compound is:
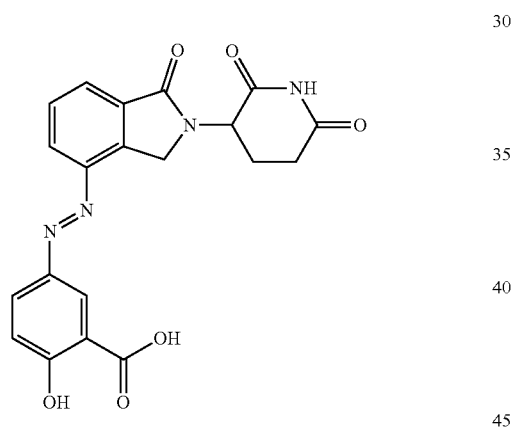
30
35
40
45
or a pharmaceutically acceptable salt, tautomer or stereoisomer thereof.
In some embodiments, a compound within the scope of formula I has the following tautomers:
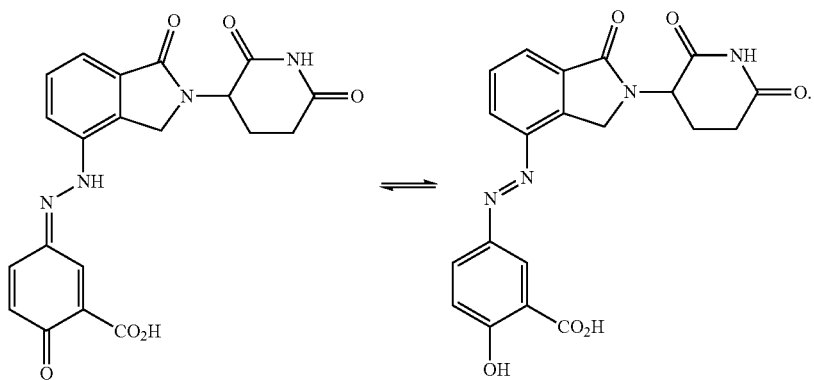 [SMILES: O=C1CCC(N2Cc3c(N/N=C4/C=CC(=O)C(C(=O)O)=C4)cccc3C2=O)C(=O)N1 ; O=C1CCC(N2Cc3c(/N=N/c4ccc(O)c(C(=O)O)c4)cccc3C2=O)C(=O)N1]

In some embodiments, the compound is:

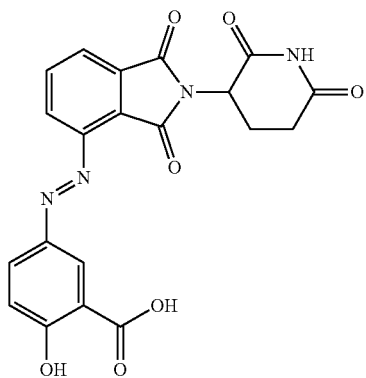 [SMILES: O=C1CCC(N2C(=O)c3cccc(/N=N/c4ccc(O)c(C(=O)O)c4)c3C2=O)C(=O)N1]

or a pharmaceutically acceptable salt, tautomer or stereoisomer thereof.

In some embodiments, a compound within the scope of formula I has the following tautomers:

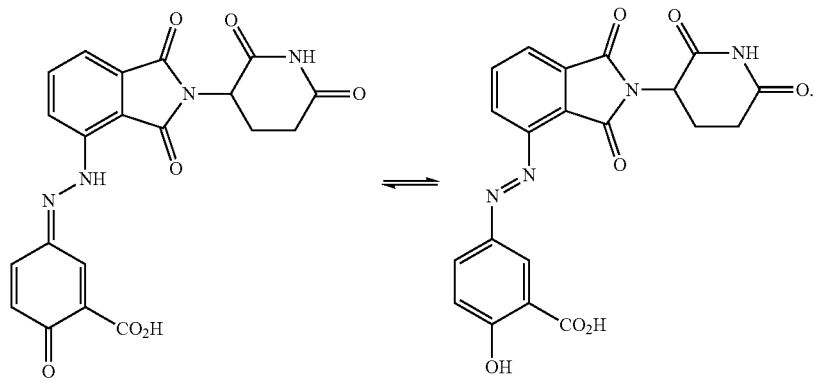 [SMILES: O=C1CCC(N2C(=O)c3cccc(N/N=C4/C=CC(=O)C(C(=O)O)=C4)c3C2=O)C(=O)N1 ; O=C1CCC(N2C(=O)c3cccc(/N=N/c4ccc(O)c(C(=O)O)c4)c3C2=O)C(=O)N1]

In a further aspect provided herein is a pharmaceutical composition comprising a compound as disclosed herein and pharmaceutically acceptable carrier.

In another aspect, provided herein is a compound as disclosed herein for use as a medicament.

In some embodiments, a compound as provided herein or a pharmaceutically acceptable salt or stereoisomer thereof, is for use in a method to treat ulcerative colitis, wherein the method comprises administering 1-3000 mg of the compound once or twice daily by the oral route.

In some embodiments, a compound as provided herein or a pharmaceutically acceptable salt or stereoisomer thereof, is for use in a method to treat plaque psoriasis, wherein the method comprises administering 1-3000 mg of the compound once or twice daily by the oral route.

In some embodiments, a compound as provided herein or a pharmaceutically acceptable salt or stereoisomer thereof, is for use in a method to treat psoriatic arthritis, wherein the method comprises administering 1-3000 mg of the compound once or twice daily by the oral route.

In some embodiments, a compound as provided herein or a pharmaceutically acceptable salt or stereoisomer thereof, is for use in a method to treat cancer, wherein the method comprises administering 1-3000 mg once or twice daily by the oral route.

In one embodiment, the cancer is colorectal cancer.

In some embodiments, a compound as provided herein or a pharmaceutically acceptable salt or stereoisomer thereof, is for use in a method to treat inflammatory bowel disease, wherein the method comprises administering 1-3000 mg once or twice daily by the oral route.

In some embodiments, a compound as provided herein or a pharmaceutically acceptable salt or stereoisomer thereof, is for use in a method to treat Crohn's disease, wherein the method comprises administering 1-3000 mg once or twice daily by the oral route.

In some embodiments, a compound as provided herein or a pharmaceutically acceptable salt or stereoisomer thereof, is for use in a method to treat cancer, wherein the method comprises administering 1-3000 mg of the compound as a pharmaceutically acceptable salt.

In one embodiment, the cancer is colorectal cancer.

In some embodiments, a compound as provided herein or a pharmaceutically acceptable salt or stereoisomer thereof, is for use in a method to treat ulcerative colitis, wherein the method comprises administering 1-3000 mg of the compound as a pharmaceutically acceptable salt.

In some embodiments, a compound as provided herein or a pharmaceutically acceptable salt or stereoisomer thereof, is for use in a method to treat plaque psoriasis, wherein the method comprises, administering 1-3000 mg of the compound as a pharmaceutically acceptable salt.

In some embodiments, a compound as provided herein or a pharmaceutically acceptable salt or stereoisomer thereof, is for use in a method to treat psoriatic arthritis, wherein the method comprises, administering 1-3000 mg of the compound as a pharmaceutically acceptable salt.

In some embodiments, a compound as provided herein or a pharmaceutically acceptable salt or stereoisomer thereof, is for use in a method to treat inflammatory bowel disease, wherein the method comprises, administering 1-3000 mg of the compound as a pharmaceutically acceptable salt.

In some embodiments, a compound as provided herein or a pharmaceutically acceptable salt or stereoisomer thereof, is for use in a method to treat Crohn's disease, wherein the method comprises, administering 1-3000 mg of the compound as a pharmaceutically acceptable salt.

In some embodiments, the method comprises administering the compound once daily by the oral route.

In some embodiments, the method comprises administering the compound at a dose of 20 mg/kg or 60 mg/kg once daily by the oral route.

In general, the technical teaching of one embodiment can be combined with that disclosed in other embodiments provided herein.

A "tautomer" refers to a proton shift from one atom of a molecule to another atom of the same molecule, for example, as shown for the structures above. Embodiments thus include tautomers of the disclosed compounds.

The disclosure also provides methods for treating or ameliorating ulcerative colitis comprising administering to a subject therapeutically effective amounts of compounds of the present disclosure or pharmaceutically acceptable salts thereof.

Without being bound by theory, it is believed that in the colon the compounds of the present disclosure are metabolized to produce aminosalicylic acid (5-ASA) and a PDE4 inhibitor, each of which is therapeutic in treating UC. Additionally, because the compounds of the present disclosure are believed to be primarily metabolized in the colon, the 5-ASA and PDE4 inhibitors are not administered systemically. Rather, they are delivered locally to the colon where treatment is needed, thereby limiting off-target affects and allowing for lower dosages and improved safety and efficacy.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The terms "a," "an," "the" and similar referents used herein (for example in the context of the following embodiments) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the terms "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

Words using the singular or plural number also include the plural and singular number, respectively. Additionally, the words "herein," "above," and "below" and words of similar import, when used in this application, shall refer to this application as a whole and not to any particular portions of the application.

As used herein, the term "subject", "individual," or "patient," used interchangeably, refers to any animal, including mammals, such as mice, rats, other rodents, rabbits, dogs, cats, birds, swine, horses, livestock (e.g., pigs, sheep, goats, cattle), primates or humans. In one embodiment, the subject is a human. In one embodiment, the individual is a human. In one embodiment, the patient is a human.

As used here, a subject "in need thereof" refers to a subject that has the disorder or disease to be treated or is predisposed to or otherwise at risk of developing the disease or disorder.

As used here, the terms "treatment" and "treating" means: inhibiting the progression the disease; prophylactic use for example, preventing or limiting development of a disease, condition or disorder in an individual who may be predisposed or otherwise at risk to the disease, condition or disorder but does not yet experience or display the pathology or symptomatology of the disease; inhibiting the disease; for example, inhibiting a disease, condition or disorder in an individual who is experiencing or displaying the pathology or symptomatology of the disease, condition or disorder; ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or eliciting the referenced biological effect.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The pharmaceutical compositions described herein generally comprise a combination of one or more of compounds described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In one embodiment, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intra-tracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl and propylhydroxy benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 1 to about 3000 mg, or 5 to about 100 mg, or about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. In some embodiments, a compound as provided herein or a pharmaceutically acceptable salt or stereoisomer thereof, is administered at a dose of 1-3000 mg. In certain embodiments, a compound as provided herein or a pharmaceutically acceptable salt or stereoisomer thereof is administered at a dose of 1-3000 mg. In an further embodiments, a compound as provided herein or a pharmaceutically acceptable salt or stereoisomer thereof is administered at a dose of 1-3000 mg once or twice daily by the oral route. In some embodiments, a compound as provided herein or a pharmaceutically acceptable salt or stereoisomer thereof is administered at a dose of 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, or 100 mg/day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound described herein. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose response curves derived from in vitro or animal model test systems.

The compounds described herein can also be formulated in combination with one or more additional active ingredients which can include any pharmaceutical agent such as vitamin B2, anti-viral agents, vaccines, antibodies, immune enhancers, immune suppressants, anti-inflammatory agents and the like.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$ alkoxycarbonyloxy and OC(O)$C_1$-$C_6$ alkyl indicate the same functionality; similarly arylalkyl and alkylaryl indicate the same functionality.

"Amidinyl" refers to a radical of the form —(C=NR$_a$)NR$_b$R$_c$, wherein R$_a$, R$_b$ and R$_c$ are each independently H or $C_1$-$C_6$ alkyl.

"Amino" refers to the —NH$_2$ radical.

"Aminylsulfone" refers to the —S(O)$_2$NH$_2$ radical.

"Carboxy" or "carboxyl" refers to the —CO$_2$H radical.

"Cyano" refers to the —CN radical.

"Guanidinyl" refers to a radical of the form —NR$_d$(C=NR$_a$)NR$_b$R$_c$, wherein R$_a$, R$_b$, R$_c$ and R$_d$ are each independently H or $C_1$-$C_6$ alkyl.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). "Amidinylalkyl" refers to an alkyl group comprising at least one amidinyl substituent. "Guanidinylalkyl" refers to an alkyl group comprising at least one guanidinyl substituent. Unless stated otherwise specifically in the specification, an alkyl, amidinylalkyl and/or guanidinylalkyl group is optionally substituted.

"Deuteroalkyl" refers to an alkyl that is substituted by one or more deuterium atoms.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkylcycloalkyl" refers to a radical of the formula —R$_b$R$_d$ where R$_b$ is cycloalkyl as defined herein and R$_d$ is an alkyl radical as defined above. Unless stated otherwise specifically in the specification, an alkylcycloalkyl group is optionally substituted.

"Alkoxy" refers to a radical of the formula —OR$_a$ where R$_a$ is an alkyl radical as defined above containing one to twelve carbon atoms. "Amidinylalkyloxy" refers to an alkoxy group comprising at least one amidinyl substituent on the alkyl group. "Guanidinylalkyloxy" refers to an alkoxy group comprising at least one guanidinyl substituent on the alkyl group.

"Alkylcarbonylaminylalkyloxy" refers to an alkoxy group comprising at least one alkylcarbonylaminyl substituent on the alkyl group. "Heterocyclylalkyloxy" refers to an alkoxy group comprising at least one heterocyclyl substituent on the alkyl group. "Heteroarylalkyloxy" refers to an alkoxy group comprising at least one heteroaryl substituent on the alkyl group. "Aminylalkyloxy" refers to an alkoxy group comprising at least one substituent of the form —$NR_aR_b$, where $R_a$ and $R_b$ are each independently H or $C_1$-$C_6$ alkyl, on the alkyl group. Unless stated otherwise specifically in the specification, an alkoxy, amidinylalkyloxy, guanidinylalkyloxy, alkylcarbonylaminyl, heterocyclylalkyloxy, heteroarlyalkyloxy and/or aminylalkyloxy group is optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above containing one to twelve carbon atoms. Unless stated otherwise specifically in the specification, an alkoxyalkyl group is optionally substituted.

"Alkoxycarbonyl" refers to a radical of the formula —C(=O)$OR_a$ where $R_a$ is an alkyl radical as defined above containing one to twelve carbon atoms. Unless stated otherwise specifically in the specification, an alkoxycarbonyl group is optionally substituted.

"Alkylphosphoryl" refers to a radical of the formula —P(=O)($R_a$) where each $R_a$ is independently an alkyl radical as defined above. Unless stated otherwise specifically in the specification, an alkylphosphoryl group is optionally substituted.

"Alkylphosphorylaminyl" refers to a radical of the formula —$NR_b$P(=O)($R_a$) where each $R_a$ is independently an alkyl radical as defined above and $R_b$ is H or an alkyl radical as defined above. Unless stated otherwise specifically in the specification, an alkylphosphorylaminyl group is optionally substituted.

"Aryloxy" refers to a radical of the formula —$OR_a$ where $R_a$ is an aryl radical as defined herein. Unless stated otherwise specifically in the specification, an aryloxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. A "haloalkylaminyl" group is an alkylaminyl group comprising at least one halo substituent on the alkyl group. A "hydroxylalkylaminyl" group is an alkylaminyl group comprising at least one hydroxyl substituent on the alkyl group. An "amidinylalkylaminyl" group is an alkylaminyl group comprising at least one amidinyl substituent on the alkyl group. A "guanidinylalkylaminyl" group is an alkylaminyl group comprising at least one guanidinyl substituent on the alkyl group. Unless stated otherwise specifically in the specification, an alkylaminyl, haloalkylaminyl, hydroxylalkylaminyl, amidinylalkylaminyl and/or guanidinylalkylaminyl group is optionally substituted.

"Aminylalkyl" refers to an alkyl group comprising at least one aminyl substituent (—$NR_aR_b$ wherein $R_a$ and $R_b$ are each independently H or $C_1$-$C_6$ alkyl). The aminyl substituent can be on a tertiary, secondary or primary carbon. Unless stated otherwise specifically in the specification, an aminylalkyl group is optionally substituted.

"Aminylalkylaminyl" refers to a radical of the formula —$NR_aR_b$ wherein $R_a$ is H or $C_1$-$C_6$ alkyl and $R_b$ is aminylalkyl. Unless stated otherwise specifically in the specification, an aminylalkylaminyl group is optionally substituted.

"Aminylalkoxy" refers to a radical of the formula —$OR_aNH_2$ wherein $R_a$ is alkylene. Unless stated otherwise specifically in the specification, an aminylalkoxy group is optionally substituted.

"Alkylaminylalkoxy" refers to a radical of the formula —$OR_aNR_bR_c$ wherein $R_a$ is alkylene and $R_b$ and $R_c$ are each independently H or $C_1$-$C_6$ alkyl, provided one of $R_b$ or $R_c$ is $C_1$-$C_6$ alkyl. Unless stated otherwise specifically in the specification, an alkylaminylalkoxy group is optionally substituted.

"Alkylcarbonylaminyl" refers to a radical of the formula —NH(C=O)$R_a$ where $R_a$ is an alkyl radical as defined above containing one to twelve carbon atoms. Unless stated otherwise specifically in the specification, an alkylcarbonylaminyl group is optionally substituted. An alkenylcarbonylaminyl is an alkylcarbonylaminyl containing at least one carbon-carbon double bond. An alkenylcarbonylaminyl group is optionally substituted.

"Alkylcarbonylaminylalkoxy" refers to a radical of the formula
—$OR_b$NH(C=O)$R_a$ where $R_a$ is an alkyl radical as defined above containing one to twelve carbon atoms and $R_b$ is alkylene. Unless stated otherwise specifically in the specification, an alkylcarbonylaminylalkoxy group is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Aminylcarbonyl" refers to a radical of the formula —C(=O)$R_aR_b$ where $R_a$ and $R_b$ are each independently H or alkyl. Unless stated otherwise specifically in the specification, an aminylcarbonyl group is optionally substituted.

"Alkylaminylcarbonyl" refers to a radical of the formula —C(=O)$NR_aR_b$, where $R_a$ and $R_b$ are each independently H or alkyl, provided at least one of $R_a$ or $R_b$ is alkyl. Unless stated otherwise specifically in the specification, an alkylaminylcarbonyl group is optionally substituted.

"Aminylcarbonylalkyl" refers to a radical of the formula —$R_cC$(=O)$NR_aR_b$, where $R_a$ and $R_b$ are each independently H or alkyl and $R_c$ is alkylene. Unless stated otherwise specifically in the specification, an aminylcarbonylalkyl group is optionally substituted.

"Aminylcarbonycycloalkylalkyl" refers to a radical of the formula —$R_cC$(=O)$NR_aR_b$, where $R_a$ and $R_b$ are each independently H or alkyl and $R_c$ is cycloalkyl. Unless stated otherwise specifically in the specification, an aminylcarbonylcycloalkyl group is optionally substituted.

"Aryl" refers to a carbocyclic ring system radical comprising 3 to 18 carbon atoms and at least one aromatic ring. For purposes of embodiments of this disclosure, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group is optionally substituted.

"Arylalkyloxy" refers to a radical of the formula —$OR_b$—$R_c$ where $R_b$ is an alkylene chain as defined above and $R_c$ is one or more aryl radicals as defined above, for example, benzyl, diphenylmethyl and the like. Unless stated otherwise specifically in the specification, an arylalkyloxy group is optionally substituted.

"Arylalkylaminyl" refers to a radical of the formula —N($R_a$)$R_b$—$R_c$ where $R_a$ is H or $C_1$-$C_6$ alkyl, $R_b$ is an alkylene chain as defined above and $R_c$ is one or more aryl radicals as defined above, for example, benzyl, diphenylmethyl and the like. Unless stated otherwise specifically in the specification, an arylalkylaminyl group is optionally substituted.

"Carboxyalkyl" refers to a radical of the formula —$R_b$—$R_c$ where $R_b$ is an alkylene chain as defined above and $R_c$ is a carboxyl group as defined above. Unless stated otherwise specifically in the specification, carboxyalkyl group is optionally substituted.

"Cyanoalkyl" refers to a radical of the formula —$R_b$—$R_c$ where $R_b$ is an alkylene chain as defined above and $R_c$ is a cyano group as defined above. Unless stated otherwise specifically in the specification, a cyanoalkyl group is optionally substituted.

"Carbocyclic" or "carbocycle" refers to a ring system, wherein each of the ring atoms are carbon.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

"Cyanocycloalkyl" refers to a radical of the formula —$R_b$—$R_c$ where $R_b$ is cycloalkyl and $R_c$ is a cyano group as defined above. Unless stated otherwise specifically in the specification, a cyanocycloalkyl group is optionally substituted.

"Cycloalkylaminylcarbonyl" refers to a radical of the formula

—C(=O)N$R_a$$R_b$, where $R_a$ and $R_b$ are each independently H or cycloalkyl, provided at least one of $R_a$ or $R_b$ is cycloalkyl. Unless stated otherwise specifically in the specification, n-cycloalkylaminylcarbonyl group is optionally substituted.

"Cycloalkylalkyl" refers to a radical of the formula —$R_b$$R_d$ where $R_b$ is an alkylene chain as defined above and $R_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A "perhaloalkyl" is an alkyl radical, as defined above, wherein each H atom is replaced with a halogen. Unless stated otherwise specifically in the specification, a haloalkyl group is optionally substituted.

"Haloalkoxy" refers to a radical of the formula —O$R_a$ where $R_a$ is a haloalkyl radical as defined herein containing one to twelve carbon atoms. Unless stated otherwise specifically in the specification, a haloalkoxy group is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. "Heterocyclyloxy" refers to a heterocyclyl group bound to the remainder of the molecule via an oxygen bond (—O—). "Heterocyclylaminyl" refers to a heterocyclyl group bound to the remainder of the molecule via a nitrogen bond (—N$R_a$—, where $R_a$ is H or $C_1$-$C_6$ alkyl). Unless stated otherwise specifically in the specification, a heterocyclyl, heterocyclyloxy and/or heterocyclylaminyl group is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group is optionally substituted.

"Heterocyclylalkyl" refers to a radical of the formula —$R_b$$R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heterocyclylalkyloxy" refers to a radical of the formula —O$R_b$$R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyloxy group is optionally substituted.

"Heterocyclylalkylaminyl" refers to a radical of the formula —N($R_c$)$R_b$$R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom, $R_c$ is H or $C_1$-$C_6$ alkyl. Unless stated otherwise specifically in the specification, a heterocyclylalkyloxy group is optionally substituted.

"Heteroaryl" refers to a 5- to 14-membered ring system radical comprising hydrogen atoms, one to thirteen ring carbon atoms, one to six ring heteroatoms selected from the group consisting of nitrogen, oxygen and sulfur, and at least one aromatic ring comprising a heteroatom. For purposes of embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). "Heteroaryloxy" refers to a heteroaryl group bound to the remainder of the molecule via an oxygen bond (—O—). "Heteroarylaminyl" refers to a heteroaryl group bound to the remainder of the molecule via a nitrogen bond (—$NR_a$—, where $R_a$ is H or $C_1$-$C_6$ alkyl). Unless stated otherwise specifically in the specification, a heteroaryl, heteroaryloxy and/or heteroarylaminyl group is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group is optionally substituted.

"Heteroarylalkyloxy" refers to a radical of the formula —$OR_bR_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom. Unless stated otherwise specifically in the specification, a heteroarylalkyloxy group is optionally substituted.

"Heteroarylalkylaminyl" refers to a radical of the formula —$NR_cR_bR_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom, and $R_c$ is H or $C_1$-$C_6$ alkyl. Unless stated otherwise specifically in the specification, a heteroarylalkyloxy group is optionally substituted. "Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted. "Hydroxylalkylaminyl" is an alkylaminyl groups comprising at least one —OH substituent, which is on a primary, secondary or tertiary carbon. Unless stated otherwise specifically in the specification, a hydroxylalkylaminyl group is optionally substituted.

"Phosphate" refers to the —OP(=O)($R_a$)$R_b$ group, where $R_a$ is OH, O⁻ or $OR_c$ and $R_b$ is OH, O⁻, $OR_c$, or a further phosphate group (e.g., to form a di- or triphosphate), wherein $R_c$ is a counter ion (e.g., Na+ and the like).

"Phosphoalkoxy" refers to an alkoxy group, as defined herein, which is substituted with at least one phosphate group, as defined herein. Unless stated otherwise specifically in the specification, a phosphoalkoxy group is optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group is optionally substituted.

The term "substituted" as used herein means any of the above groups (e.g., alkyl, alkylene, alkylcycloalkyl, alkoxy, alkylphosphoryl, alkylphosphorylaminyl, amidinylalkyloxy, guanidinylalkyloxy, alkylcarbonylaminylalkyloxy, heterocyclylalkyloxy, heteroarylalkyloxy, aminylalkyloxy, alkoxyalkyl, alkoxycarbonyl, haloalkylaminyl, hydroxylalkylaminyl, amidinylalkylaminyl, guanidinylalkylaminyl, aminylalkyl, aminylalkylaminyl, aminylalkoxy, alkylaminylalkoxy aryloxy, alkylaminyl, alkylcarbonylaminyl, alkylaminylalkyl, aminylcarbonyl, alkylaminylcarbonyl, alkylcarbonylaminylalkoxy, aminylcarbonylalkyl, aminylcarbonycycloalkylalkyl, thioalkyl, aryl, aralkyl, arylalkyloxy, arylalkylaminyl, carboxyalkyl, cyanoalkyl, cycloalkyl, cycloalkyloxy, cycloalkylaminyl, cyanocycloalkyl, cycloalkylaminylcarbonyl, cycloalkylalkyl, haloalkyl, haloalkoxy, heterocyclyl, heterocyclyloxy, heterocyclylaminyl, N-heterocyclyl, heterocyclylalkyl, heterocyclylalkyloxy, heterocyclylalkylaminyl, heteroaryl, N-heteroaryl, heteroarylalkyl, heteroarylalkyloxy, heteroarylalkylaminyl, hydroxylalkylaminyl, phosphoalkoxy and/or hydroxylalkyl) wherein at least one hydrogen atom (e.g., 1, 2, 3 or all hydrogen atoms) is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_g$, —$NR_gSO_2R_h$, —OC(=O)$NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

Synthesis of Compounds

Compounds disclosed herein are synthesized according to the methods shown in scheme 1.

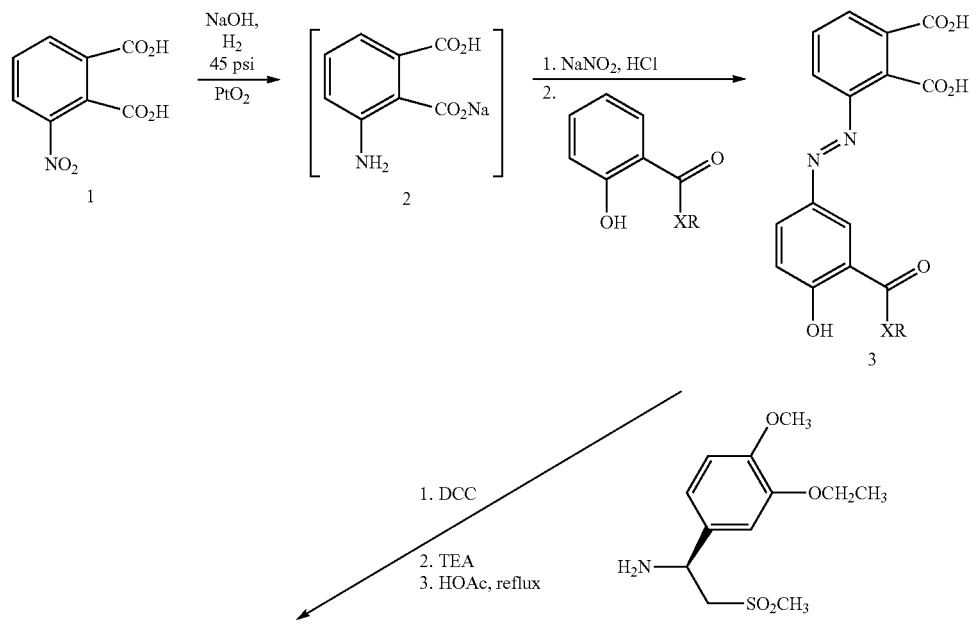

Scheme 1

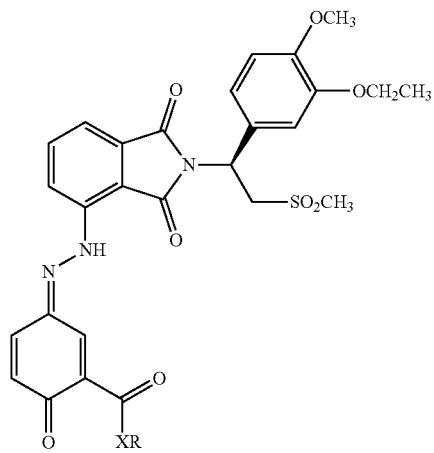

4

Treatment of 3-amino phthalic acid mono sodium salt (U.S. Pat. No. 3,951,943A) with sodium nitrite and hydrochloric acid in an aqueous solvent mixture at 0-5° C. for extended periods of time affords 3-diazo phthalic acid as an orange-colored solid. Condensation of the diazo phthalic acid with salicyclic acid esters (X=O, R=alkyl) and amide derivatives (X=NH, R=substituted alkyl or PEG side chains) is accomplished by reaction in aqueous solvents (water, THF mixtures) at high pH. These procedures produce the desired diazobenzene dicarboxylic acids 3. The side chain benzyl amine is attached to the diazobenzene via the cyclic anhydride formed by the reaction of the diacid 3 with dicyclohexyl carbodiimide (DCC) or a DCC equivalent. Ring closure and thus formation of the phthalimide is effected by heating the resulting ring-open amide in glacial acetic acid for several hours at reflux temperatures. In the case of compound 3 (X=O, R=t-butyl), the tert-butyl ester is hydrolyzed in refluxing acetic acid to afford the carboxylic acid (Scheme 1).

No attempt is made to show structural details of the disclosure in more detail than is necessary for the fundamental understanding of the disclosure, the description taken with the schemes/drawings and/or examples making apparent to those skilled in the art how the several forms of the disclosure may be embodied in practice.

EXAMPLES

Example 1

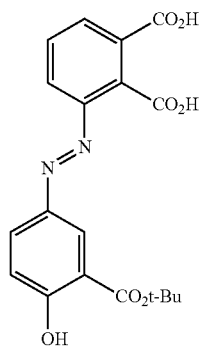 [SMILES: CC(C)(C)OC(=O)c1cc(/N=N/c2cccc(C(=O)O)c2C(=O)O)ccc1O]

Following the procedures found in U.S. Pat. No. 3,951,943A, 3-nitrophthalic acid (12.0 g, 56.84 mmol) was dissolved in 43 ml of 13% aqueous sodium hydroxide (5.59 g of NaOH in 43 ml of water) and the pH of solution was adjusted to 8.2 with dilute acetic acid (5 ml glacial acetic acid in water 3.2 ml). To this solution was added platinum oxide (65 mg), and it was subjected to hydrogenation at 45 psi of hydrogen for 12 hr. The catalyst was filtered off and the resulting 3-amino sodium phthalate solution was cooled in ice bath.

To the crude 3-amino sodium phthalate (3) solution was added concentrated hydrochloric acid (28.5 ml), at room temperature and the solution was stirred vigorously for 20 minutes (the initial clear brown solution became thick off white slurry). To this solution was added an ice cold aqueous solution (10 ml) of sodium nitrite (4.0 g, 58.0 mmol) drop wise. The resulting mixture was stirred at 0-5° C. for 45 minutes. In a separate flask tertiary butyl salicylate (2, 11.0 g, 56.84 mmol) was taken up in 10% sodium hydroxide (75 ml) and it slowly dissolved as the reaction proceeded, cooled in an ice bath with vigorous stirring (partially soluble, some white slurry formed). To this 0-5° C. stirred mixture was added a 0-5° C. solution of diazonium salt dropwise, 0-5° C. while maintaining the pH above 7.0 by adding additional 10% NaOH solution as needed. After the complete addition of diazonium salt solution, the pH was adjusted to 10.5 by adding a cold 10% sodium hydroxide (the total 10% sodium hydroxide added was 250 ml). The reddish clear reaction mixture was stirred at ice bath temperature for 3 hours and then allowed to warm room temperature. After 12 hr at room temperature, the solution was acidified with glacial acetic acid to pH 3.5, extracted with a solution of 5% methanol in dichloromethane (3×100 ml), washed with water (250 ml), dried over $MgSO_4$, filtered and concentrated under reduced pressure to yield 13.5 g of crude product which also contained unreacted tertiary butyl salicylate. The desired product (compound 4) was purified over a silica gel column chromatography with dichloromethane to 5% methanol/dichloromethane to a yellowish orange solid, 7.6 g. $^1$H NMR (300 MHz, DMSO-d6): δ 8.27 (s, 1H), 8.05 (d, J=7.8 Hz, 1H), 8.07 (d, J=9.0 Hz, 1H), 7.94 (d, J=9.0 Hz, 1H), 7.83 9d, J+7.8 Hz, 1H), 7.59-7.65 (m, 1H), 7.20 (d, J=9.0 Hz, 1H), 1.62 (s, 3H). MS: m/z=(positive ion) 408.9 (M+23)+; (negative ion) 385.1 (M−H).

Example 2 (WB301)

The azo compound prepared in Example 1 (3.85 g, 9.97 mmol) was dissolved in anhydrous $CH_2Cl_2$/acetonitrile (1:1, 70 ml) by gently warming to 50° C. with stirring for 10 minutes. The resulting orange solution was cooled in an ice bath 0-5° C. To this cold solution was added portion wise (3 times) solid 1-Ethyl-3-(3-dimethylaminopropyl) carbodiimide hydrochloride (2.48 g, 12.96 mmol) and stirred. The HPLC analysis indicated that the reaction was complete in 1 hr. To this solution was added solid (S)-1-(3-ethoxy-4-methoxyphenyl)-2-(methylsulfonyl)ethanamine (4c Pharma Scientific, 2.48 g, 9.05 mmol) followed triethylamine (2.12 g, 20.9 mmol) in acetonitrile (5 ml). The resulting red solution was stirred at 0-5° C. for 1 hr., and then at room temperature for 1 hr. The HPLC analysis indicated that the reaction was complete. The deep red solution was concentrated under reduced pressure and the residue was dissolved in 5% methanol/dichloromethane (125 ml), and washed with saturated sodium chloride solution (100 ml), and dried over $MgSO_4$, filtered and concentrated under reduced pressure. The residue was dissolved and heated (115-120° C.) with glacial acetic acid (50 ml) for 2 hr.

The reaction mixture was cooled to room temperature and poured into water (250 ml). An orange solid precipitated was filtered and washed with water (2×100 ml). The orange filtered solid was purified on a silica gel column using 5% methanol/dichloromethane to yield the desired product. $^1H$ NMR (300 MHz, DMSO-d6): δ 8.36 (d, J=2.7 Hz, 1H), 7.87-7.94 (m, 4H), 7.10 (s, 1H), 6.93, 7.05 (m, 2H), 6.83 (d, J=8.8 Hz, 1H), 5.82-5.86 (m, 1H), 4.37, m, 1H), 4.14-4.20 (m, 1H), 4.06 (q, J=7.2 Hz, 2H), 3.73 (s, 3H), 3.02 (s, 3H) 1.32 (t, J=7.0 Hz, 3H). MS: m/z=(positive ion) 590.3 (M+23, Na), 612 (M+46, 2Na) (negative ion) 566.3 (M−H).

Example 3

In Vivo Efficacy of PDE4 Inhibitor Prodrug in the Trinitrobenzenesulfonic Acid (TNBS) Rat Model of Colonic Inflammation Materials:
1. Lutrol® E400 (Sigma, Cat. 06855, lot BCBD5494V) which was stored at room temperature.
2. 1.62 g of prodrug from Example 2 (WB301), lot 2 (MW 587.12) in a clear 20 mL glass vial (orange material) which was stored at 4-8° C.
3. (−)riboflavin (Sigma, Cat. R4500, lot WXBB4048V) which was stored at −20° C.

Animals:

38 Sprague-Dawley rats (Harlan Sprague-Dawley, Inc. male, PO #599229, R #3450, 200-220 g) were received, individually examined and housed in nine cages of four rats each and one cage containing two rats. No clinical signs of disease or distress were observed. The rats were placed in quarantine with daily inspections. The rats were ear notched (SOP 800) for identification purposes, weighed (RESULTS), and sorted into four treatment groups of eight rats each based upon average body weight. The rats were individually examined and found to be free of any clinical signs of disease or distress. No deaths were recorded during the quarantine period. The rats were released to routine maintenance.

Day −1

The rats were individually examined and found to be free of any clinical signs of disease or distress. No deaths were recorded during the quarantine period.

A 16 mg/ml TNBS solution was prepared be adding 2.729 ml picrylsulfonic acid solution (1 M, FLU KA, Cat. 92822, lot CDBB6609V) to 22.271 ml de-ionized water (dH20) and 25 ml 100% ethanol (200 proof, Sigma, Cat. E7023, lot SHBH3633V).

Day 0

The rats were weighed (RESULTS), anesthetized (SOP1810) and Groups 1-4 were intra-rectally instilled with 4 ml/kg TNBS solution (64 mg/kg), the anus was pinched closed and the rat held inverted for one minute.

400 mg (−)riboflavin was dissolved in 40 ml DMSO (Sigma, Cat. D5879, lot 16K0127) by sonication in a 40° C. water bath for 20 minutes in an amber glass bottle, followed by storage at room temperature overnight to prepare a 10 mg/ml yellow solution.

135 mg NaOH (Fisher Scientific, Cat. S320, lot 066620) was dissolved in 100 ml $dH_2O$ to prepare a 1.35 mg/ml solution. 128.46 mg prednisolone 21-hemisuccinate sodium salt (Sigma, Cat. P4153, lot BCBB6136V, salt factor 1.339) was dissolved in 9.59 ml (−)riboflavin/DMSO followed by addition of 9.59 ml PEG400 (Sigma, Cat. 91893, lot BCBB7720). 28.781 aqueous NaOH was added with sonication to prepare a 2 mg/ml solution for Group 4. 44 mg WB301 was vortexed in 2.19 ml (−)riboflavin/DMSO to yield an orange solution followed by addition of 2.19 ml PEG400. 6.621 ml aqueous NaOH was added with sonication to prepare a 4 mg/ml solution for Group 1. 132 mg WB301 was vortexed in 2.19 ml (−)riboflavin/DMSO to yield an orange solution followed by addition of 2.19 ml PEG400. 6.621 ml aqueous NaOH was added with sonication to prepare a 12 mg/ml solution for Group 2. 6.6 mg apremilast was vortexed in 2.2 ml (−)riboflavin/DMSO to yield an orange solution followed by addition of 6.6 ml PEG400. 2.2 ml dH2O was added to prepare a 0.6 mg/ml solution for Group 3.

Day 1

The rats were weighed (RESULTS) and daily oral (PO, SOP 1651) dosing at 5 ml/kg was initiated as in TABLE 1.

TABLE 1

TREATMENT GROUPS

| Group | Treatment | Dose (mg/kg) |
|---|---|---|
| 1 | WB301 | 20 |
| 2 | WB301 | 60 |
| 3 | Apremilast | 3 |
| 4 | Prednisolone | 10 |

No fecal pellets were present in the bedding, indicative of loss of colonic function.

Days 2-6

The rats were weighed (RESULTS) and the animals were dosed as described above daily. WB301 and apremilast solutions were prepared fresh daily as described above.

DAY 3: Diarrhea was observed in the cages of Group 4.

DAY 4: Diarrhea was observed in the cages of Group 2. Fecal pellets were observed in the cages of Group 4, indicative of normal colonic function.

Day 7

The rats were weighed (RESULTS) anesthetized, a midline incision was made in the abdomen and the colon was evaluated for adhesions and stricture (RESULTS). The colon was removed and the length recorded (RESULTS). A midline incision was made the entire length of the colon, the contents removed and the colon weight and colon wall thickness recorded (RESULTS). A section of the colon was preserved in 20 volumes of 10% neutral buffered formalin (Richard-Allan Scientific, Cat. 5701, lot 378532, exp07/2020). The carcasses were disposed of.

Colonic Score Parameters a) Adhesions:
   1) none=0
   2) minimal=1
   3) involving several bowel loops=2
b) Strictures:
   1) none=0
   2) mild=1
   3) moderate=2
   4) severe, proximal dilatation=3
c) Ulcers:
   1) none=0
   2) linear ulceration <1 cm=1
   3) two linear ulcers <1 cm=2
   4) more sites of ulceration or one large ulcer=3
d) Wall Thickness:
   1) less than 1 mm=0
   2) 1-3 mm=1
   3) >3 mm=2

Disease Induction:

In rats dosed orally with vehicle 24 hours after instillation of 64 mg/kg TNBS through the rectum (Group 1), resulted in weight loss over the course of the study. By DAY 7, a 20% weight loss, relative to DAY 0, was recorded. At the termination of the study, the average colon weight in the diseased rats was 6.939±0.715 g and the average colon length was 12.9±0.7 cm. Severe adhesions involving multiple intestinal loops and other intraperitoneal organs, severe stricture resulting in proximal colonic distension, ulcers of 6.5±0.5 cm in length, and colonic wall thickness of 3.6±0.3 mm combined to yield an overall colonic score of 9.9±0.4 in the diseased rats.

Results:

1. Effect of Disease and Treatment on Rat Weight (g):

| | | STUDY DAY | | | | | | | | |
|---|---|---|---|---|---|---|---|---|---|---|
| | | -3 | 0 | 1 | 2 | 3 | 4 | 5 | 6 | 7 |
| Group | Rat | Weight (g) | | | | | | | | |
| 1 | 7 | 207 | 216 | 214 | 202 | 190 | 183 | 183 | 178 | 175 |
| | 13 | 211 | 214 | 207 | 191 | 184 | 180 | 175 | 170 | 162 |
| | 18 | 214 | 216 | 204 | 192 | 185 | 187 | 178 | 176 | 179 |
| | 24 | 218 | 217 | 205 | 203 | 200 | 200 | 201 | 205 | 212 |
| | 28 | 225 | 226 | 221 | 209 | 205 | 200 | 192 | 200 | 193 |
| | 30 | 218 | 225 | 224 | 222 | 220 | 226 | 201 | 200 | 193 |
| | 33 | 214 | 218 | 218 | 206 | 196 | 195 | 197 | 195 | 191 |
| | 36 | 211 | 218 | 209 | 199 | 193 | 190 | 186 | 184 | 183 |
| 2 | 2 | 214 | 217 | 206 | 205 | 199 | 192 | 196 | 207 | 220 |
| | 3 | 212 | 215 | 202 | 199 | 200 | 212 | 226 | 233 | 244 |
| | 14 | 215 | 214 | 213 | 204 | 197 | 200 | 191 | 193 | 187 |
| | 15 | 219 | 222 | 207 | 200 | 196 | 193 | 192 | 197 | 189 |
| | 21 | 208 | 208 | 203 | 195 | 184 | 179 | 182 | 184 | 178 |
| | 25 | 210 | 211 | 203 | 200 | 183 | 183 | 174 | 172 | 169 |
| | 26 | 220 | 220 | 213 | 206 | 200 | 200 | 199 | 199 | 196 |
| | 34 | 220 | 220 | 212 | 193 | 184 | 176 | 171 | 171 | 181 |
| 3 | 8 | 218 | 218 | 210 | 198 | 190 | 187 | 189 | 212 | 236 |
| | 10 | 212 | 213 | 213 | 203 | 200 | 200 | 200 | 202 | 210 |
| | 17 | 210 | 206 | 198 | 183 | 180 | 170 | 167 | 163 | 178 |
| | 19 | 219 | 220 | 214 | 203 | 198 | 188 | 182 | 176 | 178 |
| | 20 | 209 | 205 | 197 | 187 | 180 | 173 | 172 | 172 | 177 |
| | 22 | 220 | 217 | 214 | 205 | 198 | 187 | 185 | 186 | 179 |
| | 29 | 217 | 214 | 204 | 193 | 187 | 183 | 182 | 188 | 194 |
| | 35 | 213 | 217 | 206 | 214 | 225 | 234 | 244 | 250 | 256 |
| 4 | 1 | 213 | 222 | 218 | 215 | 234 | 240 | 242 | 242 | 252 |
| | 4 | 210 | 209 | 203 | 202 | 224 | 230 | 218 | 233 | 245 |
| | 5 | 213 | 213 | 206 | 189 | 181 | 182 | 182 | 177 | 181 |
| | 6 | 220 | 219 | 214 | 196 | 180 | 172 | 170 | 166 | 166 |
| | 12 | 217 | 219 | 214 | 212 | 230 | 238 | 241 | 245 | 257 |
| | 16 | 217 | 219 | 213 | 200 | 193 | 195 | 182 | 195 | 203 |
| | 27 | 219 | 216 | 212 | 211 | 205 | 200 | 203 | 216 | 222 |
| | 31 | 209 | 206 | 200 | 186 | 183 | 185 | 181 | 178 | 178 |

2. Effect of Disease and Treatment on Colonic Length, Weight, and Number of Ulcers:

| Group | Rat | Colon Weight (g) | Colon Length (cm) | Ratio (cm/g) | # Ulcers |
|---|---|---|---|---|---|
| 1 | 7 | 9.124 | 12.0 | 1.315 | 1 |
|  | 13 | 7.629 | 10.0 | 1.311 | 1 |
|  | 18 | 3.180 | 10.5 | 3.302 | 1 |
|  | 24 | 4.920 | 11.0 | 2.236 | 1 |
|  | 28 | 9.000 | 12.5 | 1.389 | 1 |
|  | 30 | 8.300 | 11.0 | 1.325 | 1 |
|  | 33 | 6.200 | 13.5 | 2.177 | 1 |
|  | 36 | 4.862 | 11.0 | 2.262 | 1 |
| 2 | 2 | 2.551 | 15.0 | 5.880 | 1 |
|  | 3 | 1.969 | 15.0 | 7.618 | 1 |
|  | 14 | 6.164 | 14.5 | 2.352 | 1 |
|  | 15 | 5.418 | 15.0 | 2.769 | 1 |
|  | 21 | 9.037 | 14.0 | 1.549 | 1 |
|  | 25 | 4.831 | 15.0 | 3.105 | 1 |
|  | 26 | 4.140 | 15.0 | 3.623 | 1 |
|  | 34 | 2.719 | 11.5 | 4.229 | 1 |
| 3 | 8 | 3.608 | 10.0 | 2.772 | 1 |
|  | 10 | 7.577 | 15.5 | 2.046 | 1 |
|  | 17 | 2.860 | 12.0 | 4.196 | 1 |
|  | 19 | 3.000 | 11.5 | 3.833 | 1 |
|  | 20 | 4.462 | 13.0 | 2.913 | 1 |
|  | 22 | 9.199 | 15.0 | 1.631 | 1 |
|  | 29 | 6.085 | 16.0 | 2.629 | 1 |
|  | 35 | 1.550 | 12.0 | 7.742 | 1 |
| 4 | 1 | 1.182 | 16.5 | 13.959 | 1 |
|  | 4 | 1.333 | 16.0 | 12.003 | 1 |
|  | 5 | 3.273 | 14.0 | 4.277 | 1 |
|  | 6 | 4.517 | 14.5 | 3.210 | 1 |
|  | 12 | 1.477 | 16.0 | 10.833 | 1 |
|  | 16 | 2.443 | 16.7 | 6.836 | 1 |
|  | 27 | 1.974 | 14.8 | 7.497 | 1 |
|  | 31 | 4.618 | 14.8 | 3.205 | 1 |

3. Effect of Disease and Treatment on Colonic Parameters:

| Group | Rat | Adhesions | Strictures | Ulcers, score | Colon Wall Thickness, score | Ulcer Length (cm) | Wall Thickness (mm) | Colonic Score |
|---|---|---|---|---|---|---|---|---|
| 1 | 7 | 2 | 3 | 3 | 2 | 7.0 | 4.0 | 10 |
|  | 13 | 2 | 3 | 3 | 2 | 6.0 | 3.7 | 10 |
|  | 18 | 1 | 3 | 3 | 1 | 5.5 | 2.5 | 8 |
|  | 24 | 1 | 2 | 3 | 1 | 6.0 | 2.5 | 7 |
|  | 28 | 2 | 3 | 3 | 2 | 6.8 | 3.7 | 10 |
|  | 30 | 2 | 3 | 3 | 2 | 6.5 | 4.0 | 10 |
|  | 33 | 1 | 3 | 3 | 2 | 6.0 | 3.5 | 9 |
|  | 36 | 1 | 3 | 3 | 2 | 6.3 | 3.2 | 9 |
| 2 | 2 | 0 | 1 | 3 | 1 | 3.5 | 2.0 | 5 |
|  | 3 | 0 | 0 | 3 | 1 | 4.0 | 2.0 | 4 |
|  | 14 | 2 | 3 | 3 | 1 | 6.0 | 2.0 | 9 |
|  | 15 | 1 | 3 | 3 | 1 | 6.0 | 3.0 | 8 |
|  | 21 | 2 | 3 | 3 | 2 | 6.5 | 4.0 | 10 |
|  | 25 | 2 | 3 | 3 | 1 | 6.7 | 3.0 | 9 |
|  | 26 | 2 | 3 | 3 | 1 | 6.5 | 2.0 | 9 |
|  | 34 | 1 | 1 | 3 | 1 | 5.5 | 2.5 | 6 |
| 3 | 8 | 1 | 1 | 3 | 1 | 6.5 | 2.5 | 6 |
|  | 10 | 2 | 3 | 3 | 2 | 6.5 | 3.5 | 10 |
|  | 17 | 1 | 1 | 3 | 2 | 5.5 | 3.5 | 7 |
|  | 19 | 1 | 1 | 3 | 2 | 6.0 | 3.7 | 7 |
|  | 20 | 1 | 3 | 3 | 1 | 6.4 | 2.5 | 8 |
|  | 22 | 2 | 3 | 3 | 2 | 8.0 | 4.0 | 10 |
|  | 29 | 2 | 3 | 3 | 1 | 7.5 | 2.5 | 9 |
|  | 35 | 0 | 0 | 3 | 1 | 4.0 | 1.5 | 4 |
| 4 | 1 | 0 | 0 | 1 | 1 | 0.5 | 1.0 | 2 |
|  | 4 | 0 | 0 | 1 | 1 | 0.5 | 1.0 | 2 |
|  | 5 | 1 | 0 | 3 | 1 | 4.0 | 2.5 | 5 |
|  | 6 | 2 | 1 | 3 | 1 | 6.5 | 3.0 | 7 |
|  | 12 | 0 | 0 | 1 | 1 | 0.5 | 1.0 | 2 |
|  | 16 | 0 | 0 | 3 | 1 | 2.5 | 1.5 | 4 |
|  | 27 | 0 | 0 | 3 | 1 | 3.0 | 1.0 | 4 |
|  | 31 | 1 | 1 | 3 | 1 | 4.5 | 3.0 | 6 |

Statistical Analysis:
1. Effect of Disease and Treatment on Average Rat Weight (g):

| Group | Statistic | STUDY DAY | | | | | | | | |
|---|---|---|---|---|---|---|---|---|---|---|
| | | −3 | 0 | 1 | 2 | 3 | 4 | 5 | 6 | 7 |
| 1 | Mean | 215 | 219 | 213 | 203 | 197 | 195 | 189 | 189 | 186 |
| | SD | 6 | 4 | 8 | 10 | 12 | 14 | 10 | 13 | 15 |
| 2 | Mean | 215 | 216 | 207 | 200 | 193 | 192 | 191 | 195 | 196 |
| | SD | 5 | 5 | 5 | 5 | 8 | 12 | 17 | 20 | 25 |
| 3 | Mean | 215 | 214 | 207 | 198 | 195 | 190 | 190 | 194 | 201 |
| | SD | 4 | 6 | 7 | 10 | 15 | 20 | 24 | 28 | 30 |
| 4 | Mean | 215 | 215 | 210 | 201 | 204 | 205 | 202 | 207 | 213 |
| | SD | 4 | 6 | 6 | 11 | 23 | 27 | 28 | 32 | 36 |

The effect of oral treatments on the rat weights is shown in FIG. 1.

2. Effect of Disease and Treatment on Average Colonic Length, Weight, and Number of Ulcers:

| Group | Statistic | Colon Weight (g) | Colon Length (cm) | Ratio (cm/g) | # Ulcers |
|---|---|---|---|---|---|
| 1 | Mean | 6.652 | 11.4 | 1.915 | 1 |
| | SD | 2.196 | 1.1 | 0.714 | 0 |
| 2 | Mean | 4.604 | 14.4 | 3.891 | 1 |
| | SD | 2.322 | 1.2 | 1.992 | 0 |
| 3 | Mean | 4.793 | 13.1 | 3.470 | 1 |
| | SD | 2.614 | 2.2 | 1.921 | 0 |
| 4 | Mean | 2.602 | 15.4 | 7.728 | 1 |
| | SD | 1.388 | 1.0 | 4.147 | 0 |

Figure 2:
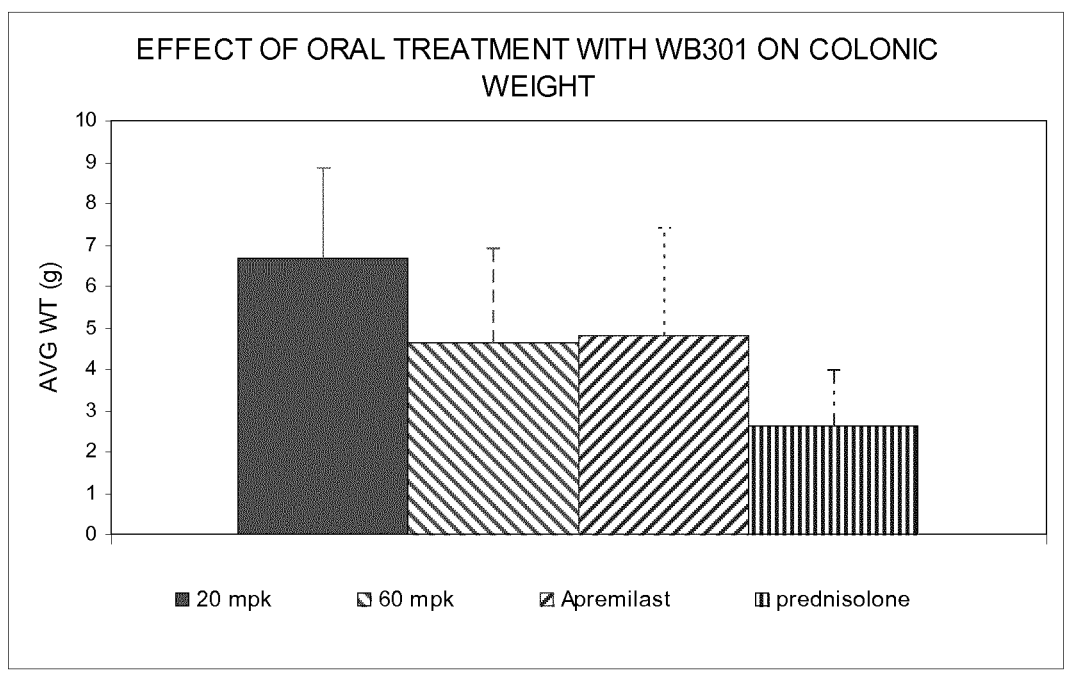
FIG. 2 shows the effect on colonic weight in an animal model following oral treatments by a prodrug according to one embodiment as compared to other therapy.
Figure 3:
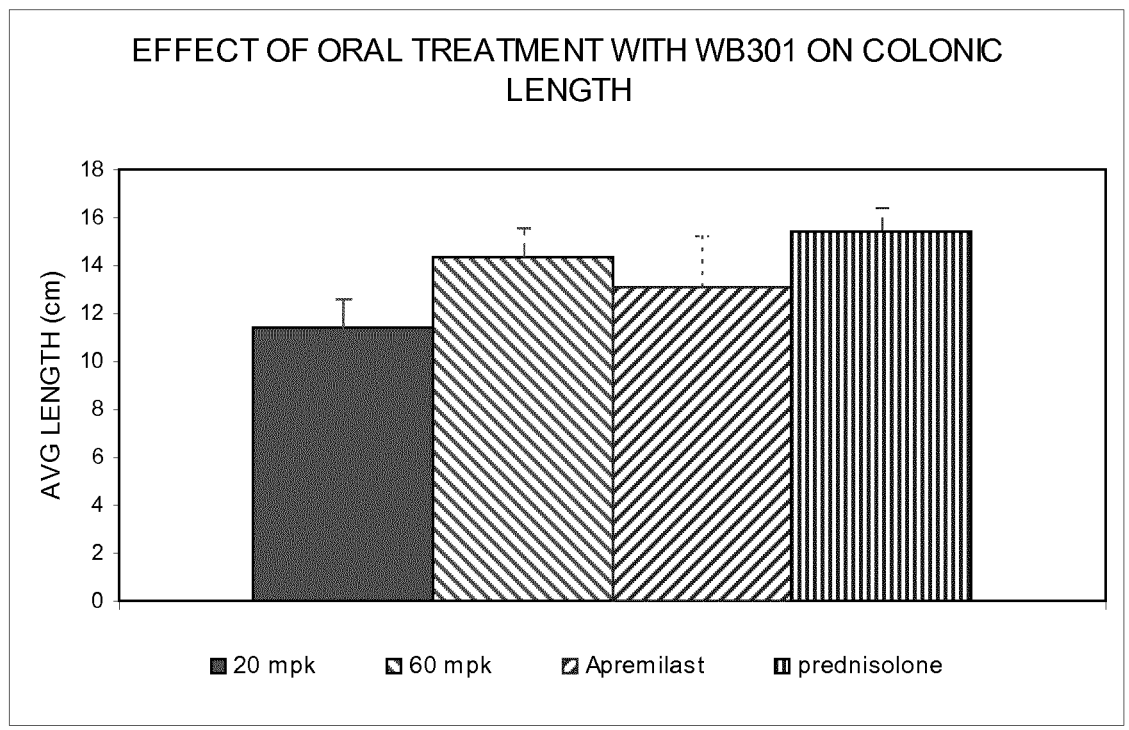
FIG. 3 shows the effect on colonic length in an animal model following oral treatments by a prodrug according to one embodiment as compared to other therapy.
Figure 4:
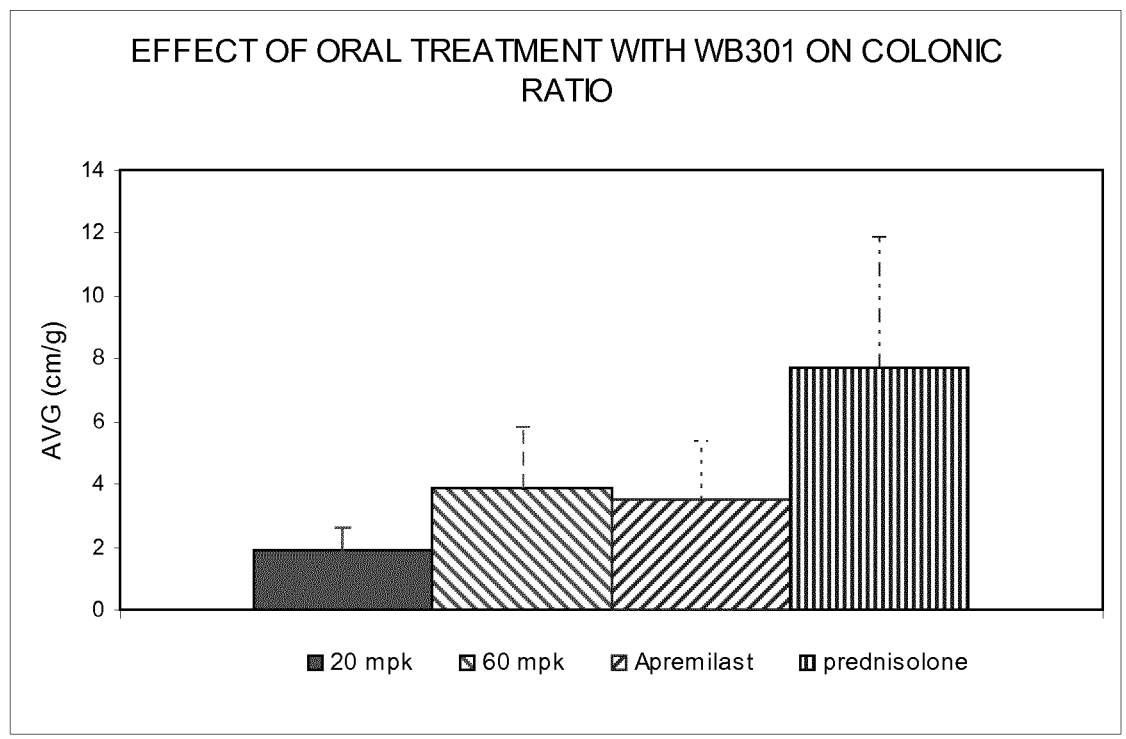
FIG. 4 shows the effect on colonic ratio in an animal model following oral treatments by a prodrug according to one embodiment as compared to other therapy.

The effect of respective oral treatments on colonic weight is shown in FIG. 2.
The effect of respective oral treatments on colonic length is shown in FIG. 3.
The effect of respective oral treatments on colonic ratio is shown in FIG. 4.

3. Effect of Disease and Treatment on Average Colonic Parameters:

| Group | Statistic | Adhesions | Strictures | Ulcers, score | Colon Wall Thickness, score | Ulcer Length (cm) | Wall Thickness (mm) | Colonic Score |
|---|---|---|---|---|---|---|---|---|
| 1 | Mean | 1.5 | 2.9 | 3.0 | 1.8 | 6.3 | 3.4 | 9.1 |
| | SD | 0.5 | 0.4 | 0.0 | 0.5 | 0.5 | 0.6 | 1.1 |
| 2 | Mean | 1.3 | 2.1 | 3.0 | 1.1 | 5.6 | 2.6 | 7.5 |
| | SD | 0.9 | 1.2 | 0.0 | 0.4 | 1.2 | 0.7 | 2.2 |
| 3 | Mean | 1.3 | 1.9 | 3.0 | 1.5 | 6.3 | 3.0 | 7.6 |
| | SD | 0.7 | 1.2 | 0.0 | 0.5 | 1.2 | 0.8 | 2.1 |
| 4 | Mean | 0.5 | 0.3 | 2.3 | 1.0 | 2.8 | 1.8 | 4.0 |
| | SD | 0.8 | 0.5 | 1.0 | 0.0 | 2.2 | 0.9 | 1.9 |

Figure 5:
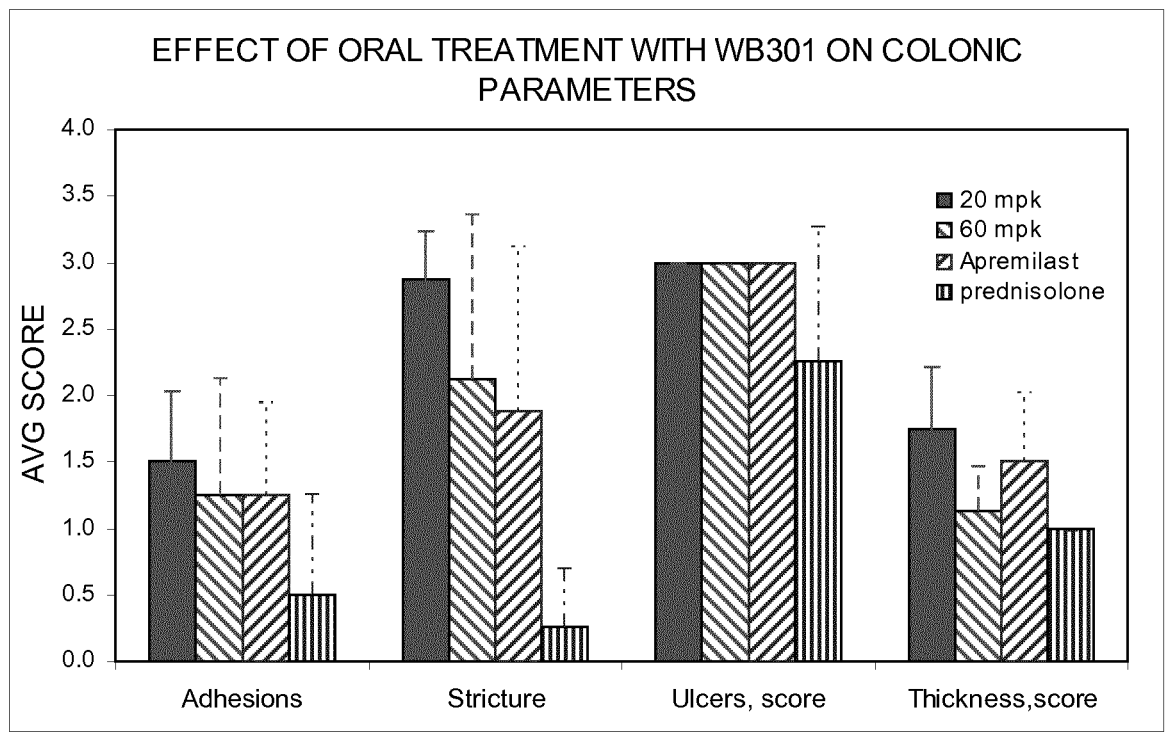
FIG. 5 shows the effect on colonic parameters in an animal model following oral treatments by a prodrug according to one embodiment as compared to other therapy.
Figure 6:
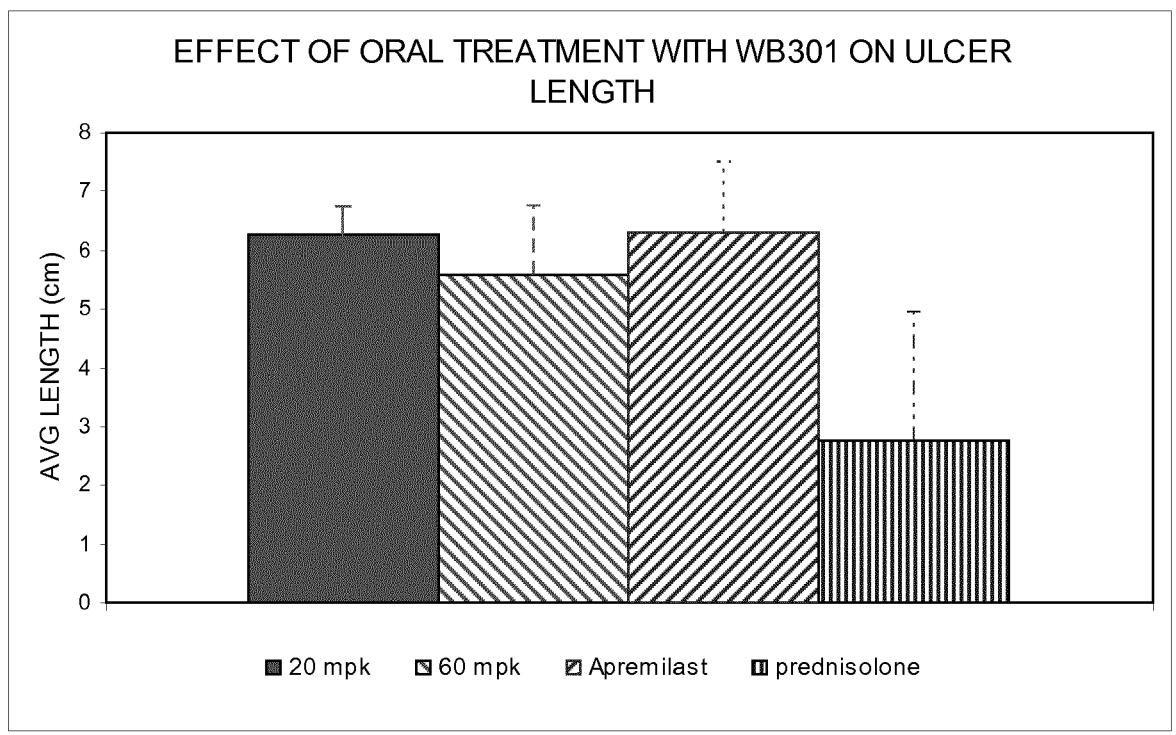
FIG. 6 shows the effect on ulcer length in an animal model following oral treatments by a prodrug according to one embodiment as compared to other therapy.
Figure 7:
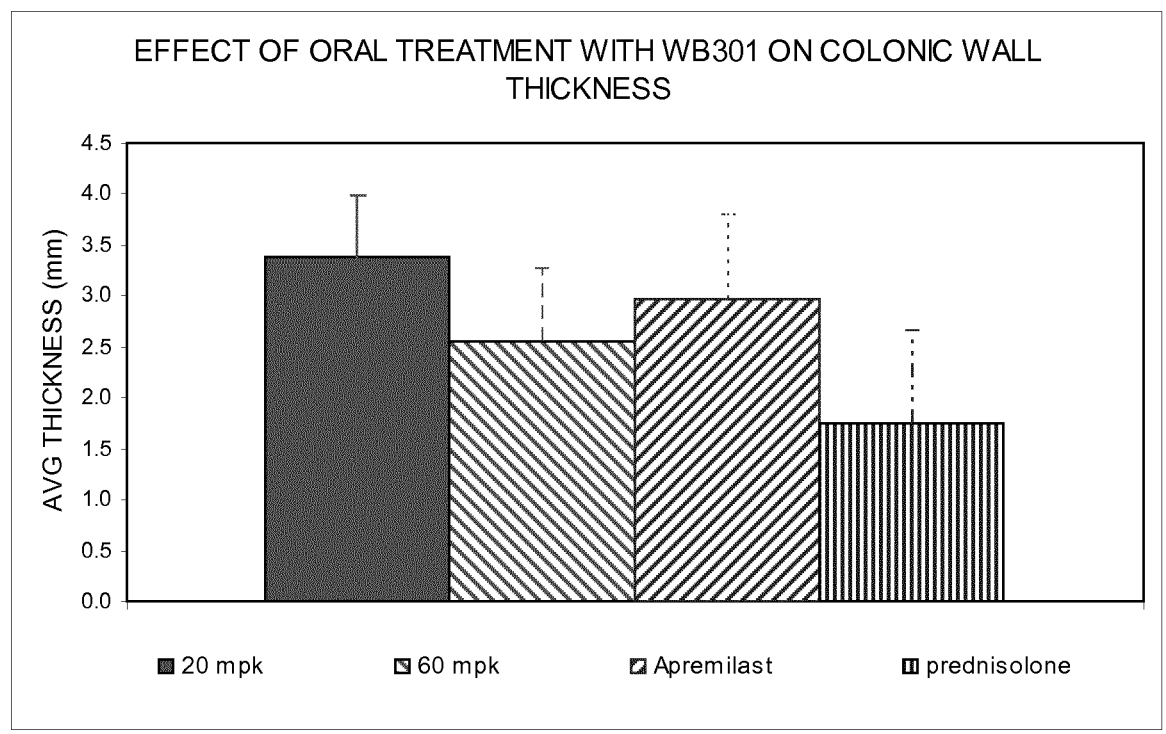
FIG. 7 shows the effect on colonic wall thickness in an animal model following oral treatments by a prodrug according to one embodiment as compared to other therapy.
Figure 8:
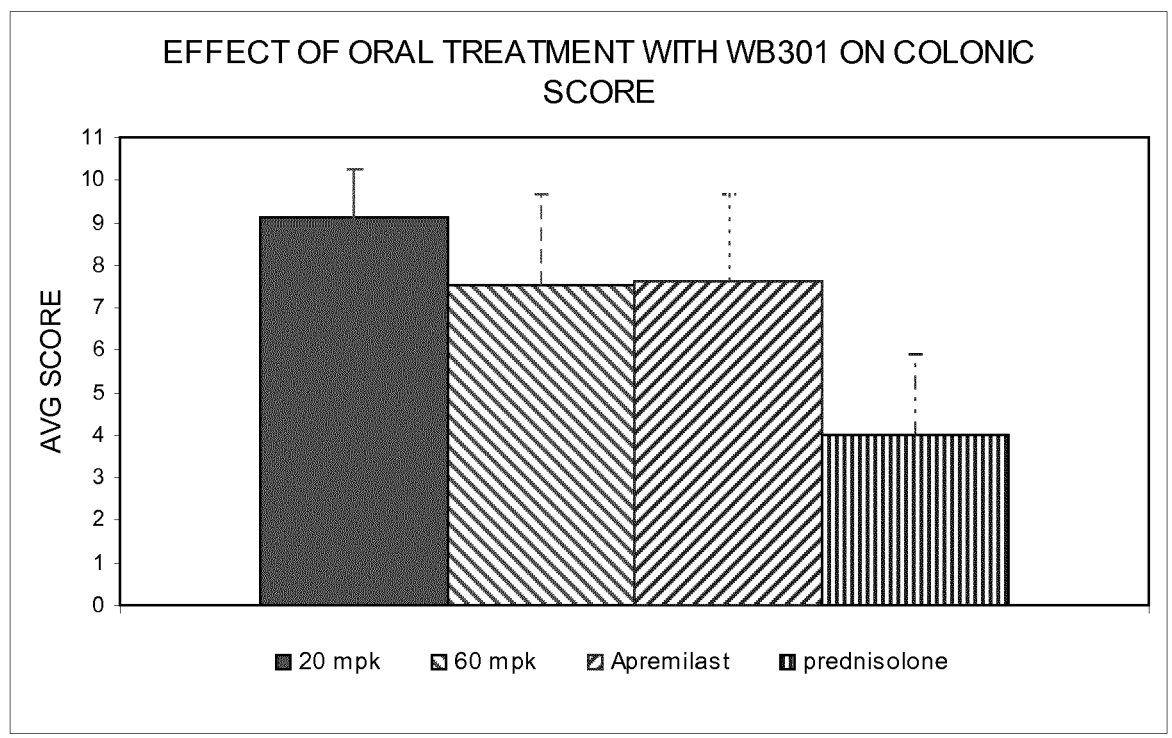
FIG. 8 shows the effect on colonic score in an animal model following oral treatments by a prodrug according to one embodiment as compared to other therapy.

Effect of respective oral treatments on colonic parameters is shown in FIG. 5.
Effect of respective oral treatments on ulcer length is shown in FIG. 6.
Effect of respective oral treatments on colonic wall thickness is shown in FIG. 7.
Effect of respective oral treatments on colonic score is shown in FIG. 8.

CONCLUSIONS

Effect of Therapeutic Treatment with WB301 (Groups 1, 2):

Once daily oral administration of soluble WB301, starting 24 hours after TNBS challenge, resulted in a dose-dependent reduction in the TNBS-induced damage. At the lowest dose (Group 1, 20 mg/kg or 20 mpk) no apparent amelioratory effect was observed (15% weight loss; colonic score=9.1). At the highest dose (Group 2, 60 mg/kg or 60 mpk) the rats began to recover from the TNBS-induced weight loss on DAY 6. Diarrhea was observed in the bedding starting on DAY 4, indicative of partial colon function. This treatment regimen also yielded an improvement of the macroscopic disease scores culminating in a 25% reduction in overall colonic score (assuming a colonic score of 10 for vehicle-treated rats).

Effect of Therapeutic Treatment with Apremilast (Group 3):

Daily oral administration of 3 mg/kg apremilast (WO2009/120167), starting 24 hours after TNBS challenge resulted in 11% body weight loss through DAY 5. Starting on DAY 6, the rats treated with apremilast began to recover from the TNBS-induced weight loss. This treatment regimen also resulted in improvement of the macroscopic disease scores culminating in a 25% reduction in overall colonic score (assuming a colonic score of 10 for vehicle-treated rats).

Effect of Therapeutic Treatment with Prednisolone (Group 4):

Daily oral administration of 10 mg/kg prednisolone, starting 24 hours after TNBS challenge resulted in an initial 9% body weight loss through DAY 4. Starting on DAY 5, the rats treated with prednisolone began to recover from the TNBS-

The invention claimed is:

1. A compound of formula (I):

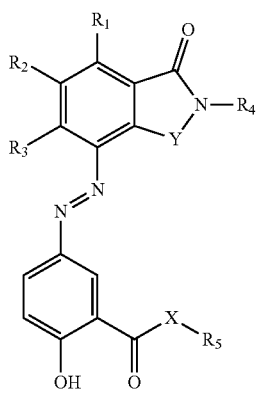

(I)

or a pharmaceutically acceptable salt tautomer or stereoisomer thereof, wherein:

X is oxygen;
Y is $CH_2$ or C=O;
$R_1$, $R_2$ and $R_3$ are hydrogen or deuterium;
$R_4$ is E or F

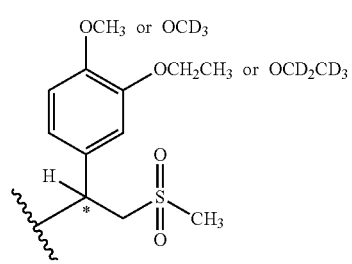

E

OR

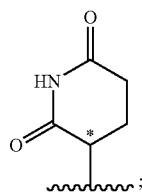

F and
$R_5$ is hydrogen.

2. The compound of claim 1, wherein the compound is:

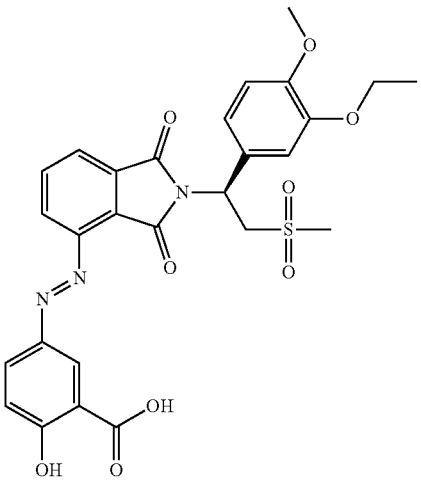 [SMILES: CCOc1cc([C@@H](CS(C)(=O)=O)N2C(=O)c3cccc(/N=N/c4ccc(O)c(C(=O)O)c4)c3C2=O)ccc1OC]

or a pharmaceutically acceptable salt, tautomer or stereoisomer thereof.

3. The compound of claim 1, wherein the compound is:

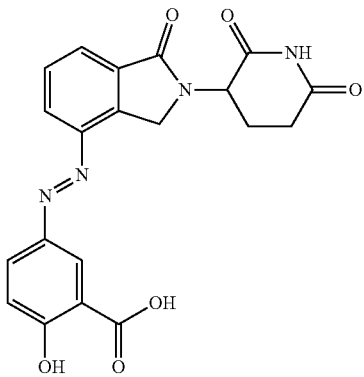 [SMILES: O=C1CCC(N2Cc3c(/N=N/c4ccc(O)c(C(=O)O)c4)cccc3C2=O)C(=O)N1]

or a pharmaceutically acceptable salt, tautomer or stereoisomer thereof.

4. The compound of claim 1, wherein the compound is:

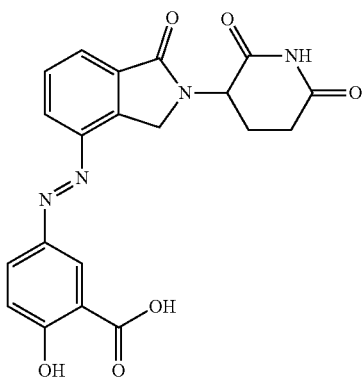 [SMILES: O=C1CCC(N2Cc3c(/N=N/c4ccc(O)c(C(=O)O)c4)cccc3C2=O)C(=O)N1]

or a pharmaceutically acceptable salt, tautomer or stereoisomer thereof.

5. A pharmaceutical composition comprising a compound of claim 1 and a pharmaceutically acceptable carrier.

6. A method to treat ulcerative colitis, plaque psoriasis, psoriatic arthritis, colorectal cancer, inflammatory bowel disease, or Crohn's disease in a patient in need thereof, wherein the method comprises administering to the patient 1-3000 mg of the compound of claim 1 dosing once or twice daily by the oral route.

7. The method of claim 6, wherein the compound is administered as a pharmaceutically acceptable salt.

8. The method of claim 6, wherein the method comprises administering the compound once daily by the oral route.

9. The method of claim 6, wherein the method comprises administering the compound at a dose of 20 mg/kg or 60 mg/kg once daily by the oral route.

* * * * *

UNITED STATES PATENT AND TRADEMARK OFFICE
CERTIFICATE OF CORRECTION

PATENT NO. : 11,639,332 B2
APPLICATION NO. : 16/970598
DATED : May 2, 2023
INVENTOR(S) : William R. Baker Page 1 of 1

It is certified that error appears in the above-identified patent and that said Letters Patent is hereby corrected as shown below:

In the Claims

Column 42, Lines 48-63, Claim 4 " 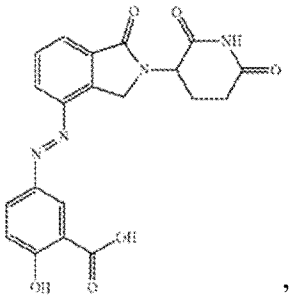 " should be

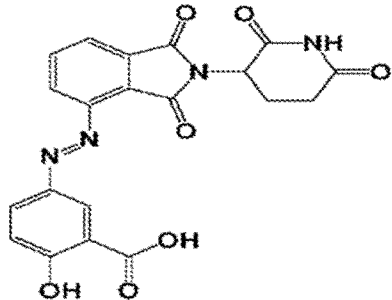

--          --.

Signed and Sealed this
Twenty-eighth Day of November, 2023

Katherine Kelly Vidal
*Director of the United States Patent and Trademark Office*